US009833430B2

(12) United States Patent
Borges et al.

(10) Patent No.: US 9,833,430 B2
(45) Date of Patent: Dec. 5, 2017

(54) NEURODEGENERATIVE DISORDERS AND METHODS OF TREATMENT AND DIAGNOSIS THEREOF

(71) Applicant: The University of Queensland, Saint-Lucia, Queensland (AU)

(72) Inventors: Karin Borges, St. Lucia (AU); Shyuan T. Ngo, St. Lucia (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 15/036,523

(22) PCT Filed: Nov. 14, 2014

(86) PCT No.: PCT/US2014/065670
§ 371 (c)(1),
(2) Date: May 13, 2016

(87) PCT Pub. No.: WO2015/073803
PCT Pub. Date: May 21, 2015

(65) Prior Publication Data
US 2016/0263071 A1 Sep. 15, 2016

Related U.S. Application Data

(60) Provisional application No. 61/904,365, filed on Nov. 14, 2013.

(51) Int. Cl.
| *A61K 31/225* | (2006.01) |
| *A61K 31/19* | (2006.01) |
| *A61K 31/194* | (2006.01) |
| *A61K 31/198* | (2006.01) |
| *A61K 31/22* | (2006.01) |
| *A61K 49/00* | (2006.01) |
| *A61K 9/00* | (2006.01) |
| *A61K 31/20* | (2006.01) |
| *A61K 31/215* | (2006.01) |

(52) U.S. Cl.
CPC ......... *A61K 31/225* (2013.01); *A61K 9/0053* (2013.01); *A61K 31/19* (2013.01); *A61K 31/194* (2013.01); *A61K 31/198* (2013.01); *A61K 31/20* (2013.01); *A61K 31/215* (2013.01); *A61K 31/22* (2013.01); *A61K 49/0008* (2013.01)

(58) Field of Classification Search
CPC .... A61K 31/225; A61K 31/20; A61K 31/215; A61K 9/0053
See application file for complete search history.

(56) References Cited

U.S. PATENT DOCUMENTS

| 4,025,649 A | 5/1977 | Taillandier et al. |
| 4,753,963 A | 6/1988 | Jandacek |
| 6,335,361 B1 | 1/2002 | Hamilton |
| 6,740,679 B1 | 5/2004 | Roe |
| 6,835,750 B1 | 12/2004 | Henderson |
| 8,399,515 B2 | 3/2013 | Roe |
| 9,468,229 B2 | 10/2016 | Mochel et al. |
| 2006/0004099 A1 | 1/2006 | Roe |
| 2006/0189545 A1 | 8/2006 | Henderson et al. |
| 2007/0123588 A1 | 5/2007 | Charles |
| 2008/0085920 A1 | 4/2008 | Donello et al. |
| 2008/0132571 A1 | 6/2008 | Roe |
| 2008/0287372 A1 | 11/2008 | Henderson |
| 2009/0253781 A1 | 10/2009 | Veech |
| 2010/0063147 A1* | 3/2010 | Durr ................ A23L 1/032 514/547 |
| 2011/0201558 A1 | 8/2011 | Roe et al. |
| 2011/0301238 A1 | 12/2011 | Borges |
| 2011/0306663 A1 | 12/2011 | Schiffmann et al. |
| 2012/0164243 A1 | 6/2012 | Rinsch et al. |
| 2012/0165405 A1 | 6/2012 | Durr et al. |
| 2013/0123359 A1 | 5/2013 | Roe |
| 2014/0364498 A1 | 12/2014 | Durr et al. |
| 2016/0374980 A1 | 12/2016 | Mochel et al. |

FOREIGN PATENT DOCUMENTS

| DE | 3032300 A1 | 4/1982 |
| EP | 1929995 | 6/2008 |
| EP | 2599482 A1 | 6/2013 |
| GB | 2104079 A | 3/1983 |
| JP | H6-287138 | 10/1994 |
| KR | 10-2001-0108173 | 12/2001 |
| WO | WO 00/45649 | 8/2000 |
| WO | WO 01/82928 | 11/2001 |
| WO | WO 2004/077938 | 9/2004 |
| WO | WO 2004/103307 | 12/2004 |
| WO | WO 2008/068230 A1 | 6/2008 |
| WO | WO 2009/018478 | 2/2009 |
| WO | WO 2009/124250 A1 | 10/2009 |
| WO | WO 2011/082111 | 7/2011 |
| WO | WO 2011/159634 | 12/2011 |
| WO | WO 2014/093901 | 6/2014 |
| WO | WO 2015/073803 | 5/2015 |

OTHER PUBLICATIONS

Stafstrom et al (Frontiers in Pharmacology, Apr. 2012, vol. 3, pp. 1-8).*
Zhao et al (PLOS ONE, vol. 7, issue 11, Nov. 2012, pp. 1-8).*
Borges et al. "Gene expression changes after seizure preconditioning in the three major hippocampal cell layers," *Neurobiology of Disease*, Jan. 18, 2007, 26:66-77.
International Search Report based on International Patent Application No. PCT/US2014/065670, mailed Feb. 12, 2015.

(Continued)

*Primary Examiner* — Sudhakar Katakam
(74) *Attorney, Agent, or Firm* — Cooley LLP

(57) ABSTRACT

This invention relates to compositions and methods for the therapy and diagnosis of neurodegenerative or neuromuscular disorders. More particularly, this invention relates to use of anaplerotic agents for treating, preventing, or delaying the onset of a neurodegenerative or neuromuscular disorder.

20 Claims, 11 Drawing Sheets

(56) References Cited

OTHER PUBLICATIONS

Supplementary European Search Report and Written Opinion for European Application No. 10841613.2, mailed Jun. 4, 2013, 10 pages.
International Search Report and Written Opinion for International Application No. PCT/US2010/062054, mailed Feb. 23, 2011, 9 pages.
Supplementary European Search Report and Written Opinion for European Application No. 13862044.8, mailed Jun. 29, 2016, 7 pages.
International Search Report and Written Opinion for International Application No. PCT/US2013/075146, mailed Mar. 11, 2014, 9 pages.
Supplemental European Search Report for European Application No. 06291873.5, mailed Jun. 12, 2007, 9 pages.
European Search Report for European Application No. 15175719.2, mailed Feb. 3, 2016, 7 pages.
International Search Report and Written Opinion for International Application No. PCT/EP2007/063181, mailed Apr. 21, 2008, 10 pages.
Andreassen, O. A. et al., "Dichloroacetate exerts therapeutic effects in transgenic mouse models of Huntington's disease," Annals of Neurology, 50(1):112-117 (Jul. 2001).
Antonini, A. et al., "Striatal glucose metabolism and dopamine D2 receptor binding in asymptomatic gene carriers and patients with Huntington's disease," Brain, 119(Pt 6):2085-2095 (1996).
Aso, E. et al., "Triheptanoin supplementation to ketogenic diet curbs cognitive impairment in APP/PS1 mice used as a model of familial alzheimer's disease," Current Alzheimer Research, 10(3):290-297 (2013).
Beal, M. F., "Energetics in the pathogenesis of neurodegenerative diseases," Trends in Neurosciences, 23(7):298-304 (Jul. 2000).
Beal, M. F. et al., "Neurochemical and histologic characterization of striatal excitotoxic lesions produced by the mitochondrial toxin 3-nitropropionic acid," J. Neurosci., 13(10):4181-4192 (1993).
Bjorkqvist, M. et al., "The R6/2 transgenic mouse model of Huntington's disease develops diabetes due to deficient b-cell mass and exocytosis," Human Molecular Genetics, 2005, 14(5):565-574, doi:10.1093/hmq/ddi053, Advance Access published on Jan. 13, 2005.
Boesgaard, T. W. et al., "Huntington's Disease does not appear to increase the risk of diabetes mellitus," Journal of Neuroendocrinology, vol. 21, Issue 9, Sep. 2009, pp. 770-776.
Borges, K. et al., "Triheptanoin—a medium chain triglyceride with odd chain fatty acids: A new anaplerotic anticonvulsant treatment?", Epilepsy Research, 100(3):239-244 (2011).
Borges, K. et al., "Anti-Epileptic Effects of Triheptanoin in Two Chronic Mouse Epilepsy Models," presented at the 24th Annual Scientific Meeting, Epilepsy Society of Australia, Perth Convention Exhibition Center (Nov. 2-4, 2009).
Borges, Slides Presented at the International Symposium on Dietary Therapies for Epilepsy and Other Neurological Disorders in Phoenix, Arizona on Mar. 8, 2008.
Borges, Slides Printed and Distributed at the International Symposium on Dietary Therapies for Epilepsy and Other Neurological Disorders in Phoenix, Arizona on Mar. 8, 2008.
Breen, C., "Unsuccessful treatment of severe pyruvate carboxylase deficiency with triheptanoin," Eur. J. Pediatr., 173:361-366 (2014).
Brockmann, K., "The expanding phenotype of GLUT1-deficiency syndrome," Brain & Development, 31:545-552 (2009).
Brunengraber, H. et al., "Anaplerotic molecules: current and future," J Inherit Metab Dis., 29:327-331 (2006).
Buckner, R. L. et al., "The Brain's Default Network, Anatomy, Function, and Relevance to Disease," Ann. N.Y. Acad. Sci., 1124:1-38 (2008).
Clarke, D. D. et al., "Circulation and energy metabolism of the brain," Chapter 31 in: Siegel G. J. et al. (eds.), Basic Neurochemistry: Molecular, Cellular and Medical Aspects, 6th edition, Philadelphia: Lippincott-Raven, 638-669 (1999).
De Almeida Rabello Oliveira et al., "Effects of short-term and long-term treatment with medium- and long-chain triglycerides ketogenic diet on cortical spreading depression in young rats," Neuroscience Letters, 434:66-70 (2008).
De Bandt, J-P. et al., "Therapeutic use of branched-chain amino acids in burn, trauma, and sepsis," J. Nutr., 136(1 Suppl):308S-313S (2006).
Deng, S. et al., "Interrelations between C4 Ketogenesis, C5 Ketogenesis, and anaplerosis in the perfused rat liver," The Journal of Biological Chemistry, 284(41):27799-27807 (Oct. 2009).
Farrer, L. A., "Diabetes mellitus in Huntington disease," Clinical Genetics 1985, 27:62-67.
Ferrante, R. J. et al., "Neuroprotective effects of creatine in a transgenic mouse model of Huntington's disease," J. Neurosci., 20(12):4389-4397 (2000).
Freeman, J. M. et al., "Ketosis and the ketogenic diet, 2010: advances in treating epilepsy and other disorders," Advances in Pediatrics, 57:315-329 (2010).
Gabuzda, D. et al., "Inhibition of energy metabolism alters the processing of amyloid precursor protein and induces a potentially amyloidogenic derivative," The Journal of Biological Chemistry, 269(18):13623-13628 (1994).
Glenner, G. G et al., "The amyloid deposits in Alzheimer's disease: their nature and pathogenesis," Appl. Pathol., 2(6):357-369 (1984).
Goedert, M. et al., "Cloning and sequencing of the cDNA encoding a core protein of the paired helical filament of Alzheimer disease: Identification as the microtubule-associated protein tau," Proc. Natl. Acad. Sci. USA, 85(11):4051-4055 (1988).
Graham, J. M. Jr., "GLUT1 deficiency syndrome as a cause of encephalopathy that includes cognitive disability, treatment-resistant infantile epilepsy and a complex movement disorder," Eur J Med Genet., 55(5):232-234 (May 2012).
Grundke-Iqbal, I. et al., "Abnormal Phosphorylation of the Microtubule-Associated Protein (tau) in Alzheimer Cytoskeletal Pathology," Proc. Natl. Acad, Sci., 83(13):4913-4917 (1986).
Guy, D. G. et al., "Effect of diets high in carbohydrate, soy oil, medium-chain triglycerides or tripelargonin on blood and liver lipid and glucose intermediates in meal-eating rats," J. Nutr., 111:1437-1445 (1981).
Hardy, J. A. et al., "Alzheimer's disease: the amyloid cascade hypothesis," Science, 256(5054):184-185 (Apr. 1992).
Henderson, S. T., "Ketone bodies as a therapeutic for Alzheimer's disease," Neurotherapeutics, 5(3):470-480 (Jul. 2008).
Henderson, S. T. et al., "Study of the ketogenic agent AC-1202 in mild to moderate Alzheimer's disease: a randomized, double-blind, placebo-controlled, multicenter trial," Nutrition & Metabolism, 6:31 (Aug. 2009) Available online; <URL: http://www.nutritionandmetabolism.com/content/6/1/31>, 25 pages.
Hurlbert, M. S. et al., "Mice transgenic for an expanded CAG repeat in the Huntington's Disease gene develop diabetes," Diabetes Mar. 1999; 48(3): 649-651. https://doi.org/10.2337/diabetes.48.3.649.
Ingle, D. L. et al., "Dietary energy value of medium-chain triglycerides," Journal of Food Science, 64(6):960-963 (1999).
IP High Court Case No. Heisei 21 (Gyoke) 10033, decided on Jan. 28, 2010, Brief History of the case, pp. 14-17.
Kashiwaya, Y. et al., "D-β-Hydroxybutyrate protects neurons in models of Alzheimer's and Parkinson's disease," PNAS, 97(10):5440-5444 (May 2000).
Kinman, R. P. et al., "Parenteral and enteral metabolism of anaplerotic triheptanoin in normal rats," Am. J. Physiol. Endocrinol Metab., 291(4): E860-E866 (2006).
Klepper, J. et al., "GLUT1 deficiency syndrome—2007 update," Dev Med Child Neurol., 49:707-716 (2007).
Klepper, J., "GLUT1 deficiency syndrome in clinical practice," Epilepsy Research, 100(3):272-277 (2012).
Kudin, A. P. et al., "Mitochondrial involvement in temporal lobe epilepsy," Experimental Neurology, 218:326-332 (2009).
Lalic, N. M. et al., "Glucose homeostasis in Huntington Disease. Abnormalities in insulin sensitivity and early-phase insulin secretion," Arch Neurol. 2008;65(4):476-480.

(56) References Cited

OTHER PUBLICATIONS

Leen, W. G. et al., "Glucose transporter-1 deficiency syndrome: the expanding clinical and genetic spectrum of a treatable disorder," Brain, 133(3):655-670 (2010).
Loscher, W., "Critical review of current animal models of seizures and epilepsy used in the discovery and development of new antiepileptic drugs," Seizure, 20:359-368 (2011).
Marin-Valencia, I. et al., "Heptanoate as a neural fuel: energetic and neurotransmitter precursors in normal and glucose transporter I-deficient (G1D) brain," Journal of Cerebral Blood Flow & Metabolism, 33(2):175-182 (2013).
Masters, C. L. et al., "Amyloid Plaque Core Protein in Alzheimer Disease and Down Syndrome," Proc. Natl. Acad. Sci., 82(12):4245-4249 (Jun. 1985).
McDonald, T. S. et al., "Alterations of hippocampal glucose metabolism by even versus uneven medium chain triglycerides," Journal of Cerebral Blood Flow & Metabolism (2014) 34, 153-160.
Milakovic, T. et al., "Mitochondrial respiration and ATP production are significantly impaired in striatal cells expressing mutant huntingtin," J. Biol. Chem., 280(35):30773-30782 (2005).
Mochel, F. et al., "Dietary anaplerotic therapy improves peripheral tissue energy metabolism in patients with Huntington's disease," European Journal of Human Genetics, 18:1057-1060 (2010).
Mochel, F. et al., "Pyruvate carboxylase deficiency: clinical and biochemical response to anaplerotic diet therapy," Molecular Genetics and Metabolism, 84:305-312 (2005).
Mochel, F. et al., "Early energy deficit in Huntington disease: identification of a plasma biomarker traceable during disease progression," Plos One, 2(7):e647 (2007). doi:10.1371/journal.prone.0000647.
Mosconi, L. et al., "Brain Glucose Hypometabolism and Oxidative Stress in Preclinical Alzheimer's Disease," Ann N Y Acad Sci. Dec. 2008; 1147:180-195. doi:10.1196/annals.1427.007.
Neal, E. G. et al., "A randomized trial of classical and medium-chain triglyceride ketogenic diets in the treatment of childhood epilepsy," Epilepsia, 50(5):1109-1117 (May 2009).
Pascual, J., "GLUT1 Transporter Deficiency Syndrome Conference," Clinical Research, Louisville, Kentucky, Jul. 15, 2010, Glut1 DS Conference, 21 pages.
Pascual, J. M. et al., "Brain glucose supply and the syndrome of infantile neuroglycopenia," Archives of Neurology, 64(4):507-513 (Apr. 2007).
Perlman, B. J. et al., "Membrane-disordering potency and anticonvulsant action of valproic acid and other short-chain fatty acids," Molecular Pharmacology, 26:83-89 (1984).
Podolsky, S. et al., "Increased frequency of diabetes mellitus in patients with Huntington's chorea," The Lancet, vol. 299, Issue 7765, Jun. 24, 1972, pp. 1356-1359. Originally published as vol. 1, Issue 7765.
Pong, A. W. et al., "Glucose transporter type I deficiency syndrome: Epilepsy phenotypes and outcomes" Epilepsia, 53(9):1503-1510 (2012).
Rangone, H. et al., "Phosphorylation of arfaptin 2 at Ser260 by Akt Inhibits PolyQ-huntingtin-induced toxicity by rescuing proteasome impairment," J. Biol. Chem., 280(23):22021-22028 (2005).
Reger, M. A. et al., "Effects of β-hydrozybutyrate on cognition in memory-impaired adults," Neurobiology of Aging, 25(3):311-314 (2004).
Reszko, A. E. et al., "Assessing the reversibility of the anaplerotic reactions of the propionyi-CoA pathway in heart and liver," J. Biol. Chem., 278(37):34959-34965 (2003).
Roe, C. R. et al., "Anaplerotic diet therapy in inherited metabolic disease: therapeutic potential," Journal of Inherited Metabolic Disease, 29(2-3):332-340 (Apr.-Jun. 2006).
Roe, C. R. et al., "Carnitine palmitoyltransferase II deficiency: successful anaplerotic diet therapy," Neurology, 71:260-264 (2008).
Roe, C. R. et al., "Treatment of cardiomyopathy and rhabdomyolysis in long-chain fat oxidation disorders using an anaplerotic odd-chain triglyceride," J Clin Invest., 110(2):259-269 (2002).

Sabatine, M. S. et al., "Metabolomic identification of novel biomarkers of myocardial ischemia," Circulation, 112(25):3868-3875 (2005).
Schneider, S. A. et al., "GLUT1 gene mutations cause sporadic paroxysmal exercise-induced dyskinesias," Movement Disorders, 24(11):1684-1688 (2009).
Segal, K. R. et al., "Lean body mass estimation by bioelectrical impedance analysis: a four-site cross-validation study," Am. J. Clin. Nutr., 47(1):7-14 (1988).
Seidner, G. et al., "GLUT-1 deficiency syndrome caused by haploinsufficiency of the blood-brain barrier hexose carrier," Nat Genet., 18:188-191 (1998).
Seyfried, T. N. et al., "Ketone strong: Emerging evidence for a therapeutic role of ketone bodies in neurological and neurodegenerative diseases," Journal of Lipid Research, 55:1815-1817 (2014).
Stepan Company, NEOBEE 895, Overview (2012), 3 pages (online), Retrieved from the Internet: <URL: http://www.stepan.com/Products/Specialty-Products/NEOBEE/NEO...>, Retrieved on: Jan. 21, 2015.
Striano, P. et al., "GLUT1 mutations are a rare cause of familial idiopathic generalized epilepsy," Neurology, 78:557-562 (2012).
Thomas, N. K. et al., "Triheptanoin in acute mouse seizure models," Epilepsy Research, 99:312-317 (2012).
Underwood, B. R. et al., "Huntington disease patients and transgenic mice have similar pro-catabolic serum metabolite profiles," Brain, 129:877-886 (2006).
Van Der Auwera, I. et al., "A ketogenic diet reduces amyloid beta 40 and 42 in a mouse model of Alzheimer's disease," Nutrition & Metabolism, 2:28 (2005).
Veech, R. L. et al., "Ketone bodies, potential therapeutic uses," IUBMB Life, 51:241-247 (2001).
Velliquette, R. A., et al., "Energy inhibition elevates β-secreatase levels and activity and is potentially amyloidogenic in APP transgenic mice: Possible early events in Alzheimer's disease pathogenesis," The Journal of Neuroscience. 25(47):10874-10883 (2005).
Verrotti, A. et al., "Glut1 deficiency: When to suspect and how to diagnose?" Eur. J. Paedeatr. Neurol., 16:3-9 (2012).
Vlaeminck, B. et al., "Milk odd- and branched-chain fatty acids in relation to the rumen fermentation pattern," Journal of Dairy Science, 89(10):3954-3964 (Oct. 2006).
Walsh, M. C. et al., "Effect of acute dietary standardization on the urinary, plasma, and salivary metabolomic profiles of healthy humans[1-3]," Am. J. Clin. Nutr., 84(3):531-539 (2006).
Wang, D. et al., "Glut-1 deficiency syndrome: clinical, genetic, and therapeutic aspects," Ann Neurol., 57:111-118 (2005).
Wang, X. et al., "Anaplerosis from heptanoate—a propionyl-CoA precursor—in mouse brain," The FASEB Journal, 21:541.12 (2007) (Abstract).
White, H. S., "Preclinical Development of Antiepileptic Drugs: Past, Present, and Future Directions," Epilepsia, 44(7):2-8 (2003).
Wikipedia, Definition of "Axona," [Retrieved on Feb. 9, 2013], Retrieved from the Internet: <URL: http://en.wikipedia/org/wiki/Axona>, 3 pages.
Wikipedia, Definition of "Fatty Acid," [Retrieved on Oct. 13, 2016], Retrieved from the Internet: <URL: https://en.wikipedia/org/wiki/Fatty_Acid>, 7 pages.
Willis, S. et al., "Anticonvulsant effects of a triheptanoin diet in two mouse chronic seizure models," Neurobiology of Disease, 40(3):565-572 (2010).
Willis, S. et al., "The effect of anaplerotic diet in mouse epilepsy models," Presentation Abstract, Program#/Poster #: 539.8/P4, Neuroscience Meeting Planner, Chicago, IL: Society for Neuroscience (2009).
Supplementary European Search Report for European Application No. 14861265.8, dated Jun. 1, 2017, 10 pages.
Glut1 Deficiency Foundation Newsletter, 2013 Glut1 Deficiency Family Conference, 5th Family Conference, Houston, Jul. 11-12, 2013, vol. 9, Spring 2013. Retrieved from the Internet: <URL::http://www.gldfoundation.org/wp-content/uploads/2013/05/Spring-2013-G1D-News.pdf>, 13 pages.

(56) References Cited

OTHER PUBLICATIONS

"Curing the Epilepsies 2013: Pathways Forward," Program Materials, Apr. 17-19, 2013, Natcher Conference Center, National Institutes of Health, Bethesda, Maryland, National Institute of Neurological Disorders and Stroke, Retrieved from the Internet: https://meetings.ninds.nih.gov/assets/2013epilepsies/CuringEpilepsies2013_PROGRAMBOOK.pdf, 204 pages.

* cited by examiner

NEURODEGENERATIVE DISORDERS AND METHODS OF TREATMENT AND DIAGNOSIS THEREOF

CROSS-REFERENCE TO RELATED APPLICATIONS

This application is a National Stage Application of International Patent Application No. PCT/US2014/065670, filed on Nov. 14, 2014, which claims the benefit of U.S. Provisional Application No. 61/904,365, filed Nov. 14, 2013, each of which is hereby incorporated by reference in its entirety.

DESCRIPTION OF THE TEXT FILE SUBMITTED ELECTRONICALLY

The contents of the text file submitted electronically herewith are incorporated herein by reference in their entireties: A computer readable format copy of the Sequence Listing (filename: ULPI_018_01_WO_SeqList_ST25.txt, date recorded Nov. 12, 2014, file size 4 kilobytes).

TECHNICAL FIELD

THIS INVENTION relates generally to compositions and methods for the therapy and diagnosis of neurodegenerative and/or neuromuscular disorders. More particularly, this invention relates to use of anaplerotic agents for treating, preventing and/or delaying the onset of a neurodegenerative and/or neuromuscular disorder.

BACKGROUND

Amyotrophic lateral sclerosis (ALS) is a neurodegenerative disease characterized by the progressive loss of motor neurons and concomitant muscle wasting. This results in increased paralysis and death within 2-5 years after diagnosis (Wijesekera and Leigh, 2009). The cause of death of motor neurons is unclear, but abnormal mitochondria, ubiquinated inclusions and neurofilament aggregates are thought to contribute.

Mitochondria are responsible for beta-oxidation of fatty acids and oxidative phosphorylation by the tricarboxylic acid (TCA) cycle and the electron transport chain, producing most of the adenosine triphosphate (ATP), the primary cellular energy source that is necessary for cell function and survival. Thus, impaired mitochondrial function in motor neurons and muscles would result in defective energy metabolism and a reduced capacity to produce ATP.

Triheptanoin, the triglyceride of heptanoate (C7 fatty acid), is a novel metabolic therapeutic that is being used in the USA to treat patients with rare genetic metabolic disorders of fatty acid oxidation (Brunengraber and Roe, 2006, Roe and Mochel, 2006). Triheptanoin provides the body with heptanoate, which as a medium chain fatty acid diffuses into the mitochondria to be metabolized to propionyl-CoA by beta-oxidation. Alternatively heptanoate is metabolized in the liver to the C5 ketones, β-hydropentanoate and β-ketopentanoate, both of which are taken up by cells by monocarboxylate transporters. Carboxylation of propionyl-CoA produces methyl-malonyl-CoA, which can be metabolized to succinyl-CoA, resulting in anaplerosis—the refilling of deficient C4 (containing four carbons) intermediates of the TCA cycle (FIG. 1). Anaplerotic enzymes include pyruvate carboxylase (Pcx) producing oxaloacetate in neurons and muscle, and most importantly in muscle glutamic pyruvic transaminases 1 and 2 (Gpt1 and 2), which catalyze the reaction pyruvate+glutamate<=>α-ketoglutarate+alanine and propionyl-CoA carboxylase subunit A (Pcca) and B (Pccb) and methylmalonyl-CoA mutase (Miut, FIG. 1).

Superoxide dismutase 1 (SOD1) protein mutations have been found in approximately 20% of patients with familial ALS and in a subset of patients with sporadic ALS. While usually found in the cytosol, mutant SOD1 accumulates within mitochondria and appears to contribute to many of the mitochondrial perturbations found in ALS (Turner and Talbot, 2008, Vucic and Kieman, 2009, Shi et al., 2010, Milani et al., 2011, Cozzolino and Carri, 2012). Mice overexpressing mutations in SOD1 are currently one of the best animal models for ALS.

SUMMARY

The present invention is based in part on the discovery that the TCA cycle plays a role in the pathogenesis of the neurodegenerative disorder ALS, wherein anaplerotic agents can influence the onset and/or progression of disease.

One form of the present invention is broadly directed to methods that utilize anaplerotic agents for treating or preventing and/or delaying the onset of neurodegenerative and/or neuromuscular disorders.

In a first aspect, the invention provides a method of treating an animal with a neurodegenerative and/or neuromuscular disease, disorder or condition, wherein said method includes the step of administering a therapeutically effective amount of one or more anaplerotic agents to said animal, to thereby treat the neurodegenerative and/or neuromuscular disease, disorder or condition in said animal.

In a second aspect, the invention provides a method of preventing and/or delaying the onset of a neurodegenerative and/or neuromuscular disease, disorder or condition, wherein said method includes the step of administering a therapeutically effective amount of one or more anaplerotic agents to said animal.

In a third aspect, the present invention provides triheptanoin for use in the preventative, prophylactic and/or therapeutic treatment of a neurodegenerative and/or neuromuscular disease, disorder or condition in an animal in need thereof.

In a fourth aspect, the present invention provides a kit for use in the preventative, prophylactic and/or therapeutic treatment of an animal with a neurodegenerative and/or neuromuscular disease, disorder or condition, said kit comprising: (i) a therapeutically effective amount of one or more anaplerotic agents; and (ii) instructions for use.

In one embodiment, the neurodegenerative and/or neuromuscular disease, disorder or condition of any one of the aforementioned aspects is a motor neuron disease (MND).

In another embodiment, the MND is amyotrophic lateral sclerosis (ALS), primary lateral sclerosis (PLS), progressive muscular atrophy (PMA), progressive bulbar palsy (PBP), pseudobulbar palsy or spinal muscular atrophy (SMA).

In yet another embodiment, the MND is amyotrophic lateral sclerosis.

In one embodiment, the anaplerotic agents of the aforementioned aspects are glutamate, glutamine, pyruvate and/or one or more precursors of propionyl-CoA.

In another embodiment, the one or more precursors of propionyl-CoA are selected from the group consisting of an uneven chain fatty acid, a triglyceride, a C5 ketone body, a phospholipid, a branched amino acid and combinations thereof.

In other embodiments, the one or more precursors of propionyl-CoA is a triglyceride or phospholipid of an uneven chain fatty acid.

In yet another embodiment, the C5 ketone body is selected from β-hydroxypentanoate and β-ketopentanoate.

In one embodiment, the precursor of propionyl-CoA is propionyl-carnitine.

In another embodiment, the branched amino acid is selected from the group consisting of valine, isoleucine and combinations thereof.

In yet another embodiment, the one or more precursors of propionyl-CoA is one or more compounds of Formula I.

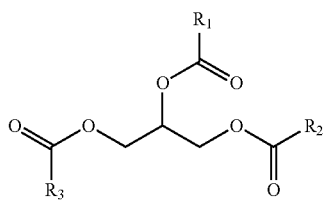

Formula I wherein $R_1$, $R_2$ and $R_3$ are independently selected from alkyl, alkenyl or alkynyl.

In one embodiment, $R_1$, $R_2$ and $R_3$ are independently selected from $C_1$ to $C_{20}$ alkyl, alkenyl or alkynyl.

In other embodiment, $R_1$, $R_2$ and $R_3$ are independently selected from $C_3$ to $C_{15}$ alkyl, alkenyl or alkynyl.

In yet another embodiment, $R_1$, $R_2$ and $R_3$ are independently selected from $C_5$ to $C_{12}$ alkyl, alkenyl or alkynyl.

In still another embodiment, $R_1$, $R_2$ and $R_3$ are independently selected from $C_6$ to $C_9$ alkyl, alkenyl or alkynyl.

In one embodiment, $R_1$, $R_2$ and $R_3$ are independently selected from methyl, ethyl, propyl, butyl, pentyl, hexyl, heptyl, octyl, nonyl, decyl, undecyl, dodecyl, tridecyl, tetradecyl and pentadecyl, inclusive of all isomers.

In another embodiment, the compound of Formula I is triheptanoin.

In other embodiments, the compound of Formula I is trinonanoin.

In yet other embodiments, the compound of Formula I is tripentanoin.

In other embodiments, the one or more anaplerotic agents are provided to the animal in an amount comprising at least about 5% of the dietary caloric intake for the animal.

In one embodiment, the one or more anaplerotic agents are provided to the animal in an amount comprising at least about 20% of the dietary caloric intake for the animal.

In another embodiment, a anaplerotic agent is provided to the animal in an amount comprising at least about 30% of the dietary caloric intake for the animal.

In yet another embodiment, the one or more anaplerotic agents are provided to the animal in an amount comprising at least about 35% of the dietary caloric intake for the animal.

In one embodiment, the animal is a mammal.

In another embodiment, the mammal is a human.

Another form of the present invention is broadly directed to methods that detect alterations, changes or differences in gene expression associated with neurodegenerative and/or neuromuscular disorders.

In a fifth aspect, the invention provides a method of determining whether an animal has, or is predisposed to, a neurodegenerative and/or neuromuscular disease, disorder or condition, wherein the method includes the step of measuring (i) the expression level of one or more nucleic acids that respectively encode enzymes associated with energy metabolism, (ii) the expression level and/or activity of said enzyme(s) and/or (iii) the level of one or more metabolites associated with energy metabolism.

In one embodiment, a decrease or reduction in the expression level of one or more nucleic acids that respectively encode enzymes associated with energy metabolism and/or a decrease or reduction in the expression level and/or activity of said enzymes and/or a decrease or reduction in the level of one or more metabolites associated with energy metabolism indicates that said animal has, or is predisposed to, the neurodegenerative and/or neuromuscular disease, disorder or condition.

In a sixth aspect, the invention provides a method of monitoring the response of an animal to treatment or prevention of a neurodegenerative and/or neuromuscular disease, disorder or condition by administration of one or more anaplerotic agents described herein, wherein the method includes the step of measuring (i) the expression level of one or more nucleic acids that respectively encode enzymes associated with energy metabolism (ii) the expression level and/or activity of said enzyme(s) and/or (iii) the level of one or more metabolites associated with energy metabolism.

In one embodiment, an increase in the expression level of one or more nucleic acids that respectively encode enzymes associated with energy metabolism and/or an increase in the expression level and/or activity of said enzymes and/or an increase in the level of one or more metabolites associated with energy metabolism indicates that said animal is responding to the administration of the one or more anaplerotic agents.

According the to the fifth and sixth aspects, the enzymes or metabolites may be selected from the group consisting of glycolytic enzymes or metabolites, TCA cycle enzymes or metabolites and anaplerotic enzymes or metabolites.

In some embodiments, the glycolytic enzyme is pyruvate dehydrogenase alpha 1, phosphoglucose isomerase (PGI), or phosphofructokinase (PFK).

In another embodiment, the TCA cycle enzymes are selected from the group consisting of oxoglutarate dehydrogenase and succinate dehydrogenase complex subunit A.

In another embodiment, the anaplerotic enzymes are selected from the group consisting of glutamate-pyruvate transaminase 1, glutamate-pyruvate transaminase 2, propionyl-CoA carboxylase subunit A and B and methylmalonyl-CoA mutase.

Throughout this specification, unless the context requires otherwise, the words "comprise", "comprises" and "comprising" will be understood to imply the inclusion of a stated integer or group of integers but not the exclusion of any other integer or group of integers.

BRIEF DESCRIPTION OF THE DRAWINGS

FIGS. 3A and 3B depict the hind limb grip strength of wild-type (FIG. 3A) or hSOD1$^{G93A}$ (FIG. 3B) mice fed with control diet (CON) or triheptanoin (TRIH) diet. The data in FIG. 3A show that no differences in grip strength were evident between triheptanoin (green open triangles, n=15) and control fed wild-type mice (black filled squares, n=12). The data in FIG. 3B show that the grip strength over time differed in triheptanoin (red crosses; n=8) vs. control diet (blue empty circles, n=5) fed high copy number transgene hSOD1$^{G93A}$ mice (p=0.04, two way ANOVA), with a significantly higher grip strength at 18 and 19.5 weeks (p<0.05 Bonferroni post-hoc test). FIG. 3C depicts the average hind limb grip strength of hSOD1$^{G93A}$ mice fed with control diet (CON) or triheptanoin (TRIH) diet. The data in FIG. 3C show that overall higher hind limb grip strength was seen in the area under the curve over time in triheptanoin fed hSOD1$^{G93A}$ mice (n=8) when compared to control fed hSOD1$^{G93A}$ mice (n=5, p<0.05; t-test). FIG. 3D depicts the onset of hind limb grip strength loss (in weeks) in hSOD1$^{G93A}$ mice fed with control diet (CON) or triheptanoin (TRIH) diet. The data in FIG. 3D show that the onset of hind limb grip strength loss was delayed by 2.8 weeks in triheptanoin-fed hSOD1$^{G93A}$ mice (n=8) when compared to control fed hSOD1$^{G93A}$ mice (n=5, p=0.002; t-test). FIG. 3E depicts the ages of hSOD1$^{G93A}$ mice at the onset of hind limb grip strength loss (in weeks) plotted against hSOD1$^{G93A}$ transgene copy numbers in those mice. The data in FIG. 3E show that the linear regressions between the age of strength loss beginning against transgene copy numbers are significantly different between the groups fed control diet ($R^2$=0.89) vs. triheptanoin ($R^2$=0.91). Specifically, the x and y intercepts are different between the two regression lines (p<0.001), but not the slopes (p=0.90).

DETAILED DESCRIPTION

Figure 1:
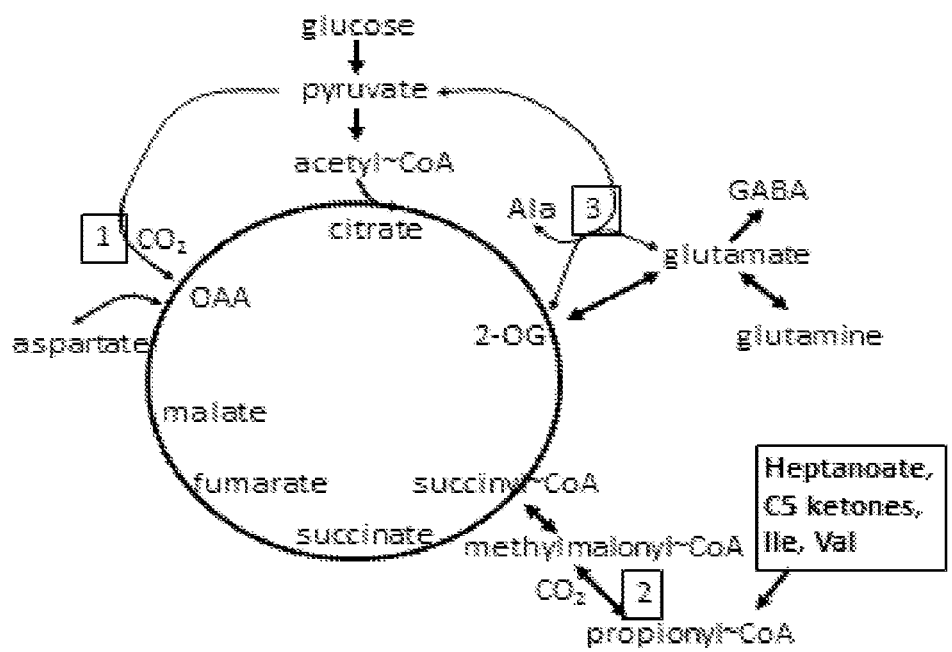
FIG. 1 depicts simplified TCA cycle and anaplerosis in CNS and muscle. The numbers enclosed in boxes ("1", "2", and "3") indicate anaplerotic pathways that can refill the C4 intermediates of the cycle: 1. pyruvate carboxylase (mostly in the CNS); 2. propionyl-CoA carboxylase; and 3. glutamic pyruvic transaminases (very important in muscle). C5 ketones, isolcucine (Ile), valine (Val), and heptanoate, are metabolised to propionyl-CoA and can therefore be anaplerotic via the propionyl-CoA carboxylation pathway. OAA—oxaloacetate, 2-OG—2-oxoglutarate.

The present invention is based, at least in part, on the discovery that the TCA cycle plays a role in the pathogenesis of the neurodegenerative disorder ALS, wherein anaplerotic agents can influence the onset and/or progression of disease.

In broad aspects, the invention relates to methods of not only treating a neurodegenerative and/or neuromuscular disease, disorder or condition, but also preventing and/or delaying the onset of a neurodegenerative and/or neuromuscular disease, disorder or condition, by administering a therapeutically effective amount of one or more anaplerotic agents to said animal.

In another aspect, the present invention provides triheptanoin for use in the preventative, prophylactic and/or therapeutic treatment of a neurodegenerative and/or neuromuscular disease, disorder or condition.

As used herein, "treating" (or "treat" or "treatment") refers to a therapeutic intervention that ameliorates a sign or symptom of a neurodegenerative and/or neuromuscular disease, disorder or condition after it has begun to develop. The term "ameliorating," with reference to a neurodegenerative and/or neuromuscular disease, disorder or condition, refers to any observable beneficial effect of the treatment. Treatment need not be absolute to be beneficial to the subject. The beneficial effect can be determined using any methods or standards known to the ordinarily skilled artisan.

As used herein, "preventing" (or "prevent" or "prevention" or "preventative") and "delaying the onset" refer to a course of action (such as administering a composition comprising a therapeutically effective amount of one or more propionyl-CoA precursors) initiated prior to the onset of a symptom, aspect, or characteristic of the neurodegenerative and/or neuromuscular disease, disorder or condition so as to prevent or delay the onset of, respectively, said symptom, aspect, or characteristic. It is to be understood that such preventing need not be absolute to be beneficial to a subject. A "prophylactic" treatment is a treatment administered to a subject who does not exhibit signs of a neurodegenerative and/or neuromuscular disease, disorder or condition, or exhibits only early signs, for the purpose of decreasing the risk of developing a symptom, aspect, or characteristic of a neurodegenerative and/or neuromuscular disease, disorder or condition. A "therapeutic" treatment is one administered to a subject who exhibits at least one symptom, aspect, or characteristic of the neurodegenerative and/or neuromuscular disease, disorder or condition so as to cure, remediate or reverse, at least in part, and/or halt or delay the progression of said symptom, aspect, or characteristic.

In the context of the present invention, by "a neurodegenerative disease, disorder or condition" is meant any disease, disorder and/or condition that comprises a progressive decline and/or deterioration in the structure, function, signalling and/or population of the neurons or neural tissue in an animal. As used herein, "a neuromuscular disease, disorder or condition" refers to any disease, disorder and/or condition that comprises a progressive decline and/or deterioration in the structure, function, signalling and/or population of the neurons or neural tissue that innervate and/or communicate, whether directly or indirectly, with the muscles of an animal.

The aetiology of a neurodegenerative and/or neuromuscular disease, disorder or condition may involve, but is not limited to, genetic mutations, protein misfolding and/or aggregation, autoimmune disorders, mitochondrial dysfunction, defective axonal transport, aberrant apoptosis and/or autophagy and elevated oxidative stress and/or reactive oxygen species (ROS) production.

Without limitation, neurodegenerative disorders include Parkinson's disease and related disorders, Huntington's disease, Alzheimer's disease and other forms of dementia, Spinocerebellar ataxia, Friedreich ataxia, Tay-Sachs disease, Lewy body disease, Prion diseases (e.g. Creutzfeldt-Jakob disease), Multiple sclerosis (MS), Pick disease, Shy-Drager syndrome, pontocerebellar hypoplasia, neuronal ceroid lipofuscinoses, Gaucher disease, neurodegeneration with brain iron accumulation, spastic ataxia/paraplegia, supranuclear palsy, mesolimbocortical dementia, thalamic degeneration, cortical-striatal-spinal degeneration, cortical-basal ganglionic degeneration, cerebrocerebellar degeneration, Leigh syndrome, post-polio syndrome, hereditary muscular atrophy, encephalitis, neuritis, hydrocephalus and the motor neuron diseases.

Further, the skilled artisan would understand that neuromuscular disorders may include Parkinson's disease and related disorders, Huntington's disease, Spinocerebellar ataxia, Friedreich ataxia, Tay Sachs disease, Lewy body disease, peripheral neuropathy, myasthenia gravis, MS, Leigh syndrome, post-polio syndrome, hereditary muscular atrophy, spastic ataxia/paraplegia and the motor neuron diseases, without limitation thereto.

In the context of the present invention, the animal with a neurodegenerative and/or neuromuscular disease, disorder or condition subject to treatment, preventative and/or therapeutic, by the claimed method has been determined to either have an existing neurodegenerative and/or neuromuscular disease, disorder or condition or be predisposed to such a disease, disorder or condition.

In one embodiment, the neurodegenerative and/or neuromuscular disease, disorder or condition of this broad aspect is a motor neuron disease.

Broadly, motor neuron diseases are a form of neurodegenerative and/or neuromuscular disorder that typically involve the motor neurons of an affected animal. As would be readily understood by a skilled artisan, motor neurons are nerve cells that control the voluntary muscles of the trunk, limbs and phalanges, as well as those muscles that influence speech, swallowing and respiration. Accordingly, the clinical symptoms of an MND may include muscle weakness and/or wasting, muscle cramps, dysphagia, slurred speech, muscle tremors/fasciculations, reduced cognition, dyspnoea, respiratory failure, fatigue and weight loss without limitation thereto. Motor neuron diseases include, but are not limited to, Amyotrophic lateral sclerosis (ALS; also known as Lou Gehrig's disease), Primary lateral sclerosis (PLS), Progressive muscular atrophy (PMA), Progressive bulbar palsy (PBP), Pseudobulbar palsy and Spinal muscular atrophy (SMA).

In light of the foregoing, the motor neuron disease may be ALS, PLS, PMA, PBP, pseudobulbar palsy or SMA.

In one embodiment, the motor neuron disease is ALS.

By "anaplerotic agent" is meant a substance that when incorporated into the TCA cycle either replenishes one or more depleted C4 (containing four carbons) intermediates of the TCA cycle or maintains or increases the level of one or more intermediates of the TCA cycle, or both.

As the skilled artisan would appreciate, the levels of TCA cycle intermediates are crucial for the normal functioning and regulation of the TCA cycle. Most TCA cycle intermediates, however, are also involved in other metabolic pathways in the cell, and consequently following their efflux from the mitochondria their respective levels may be found to be reduced in the TCA cycle. Such reductions in the levels of TCA cycle intermediates may subsequently inhibit optimal functioning of the cycle. The entry of anaplerotic agents into the TCA cycle may overcome this efflux, and thus maintain suitable levels of TCA cycle intermediates for optimal functioning of the cycle.

In one embodiment, the one or more anaplerotic agents of the current invention are citrate, alpha-keto-glutarate (2-oxoglutarate), glutamate, glutamine, succinate, fumarate, malate, pyruvate and/or one or more precursors of propionyl-CoA.

Any relevant salts (such as calcium, sodium, magnesium or potassium salts), prodrugs, analogues, derivatives, substituted and/or branched forms, precursors and derivatives of these anaplerotic agents are also contemplated within the scope of the invention. For example, salts of the present invention may include monosodium glutamate, calcium pyruvate (and calcium pyruvate monohydrate), creatine pyruvate, magnesium pyruvate, potassium pyruvate and sodium pyruvate.

One embodiment of an anaplerotic agent is a precursor of propionyl-CoA. By "precursor of propionyl-CoA" is meant a substance from which propionyl-CoA can be formed by one or more metabolic reactions taking place within a cell or tissue of an animal body.

This can include within its scope salts, prodrugs, analogues, derivatives, substituted, unsaturated, branched forms, or other uneven chain fatty acids and derivatives thereof if applicable.

Typical examples of precursors of propionyl-CoA are uneven-chain fatty acids, in particular seven-carbon fatty acids although without limitation thereto, heptanoate, triglycerides inclusive of triglycerides of an uneven chain fatty acid, a compound of Formula 1, a phospholipid comprising one or two uneven chain fatty acid(s), C5 ketone bodies (e.g. β-ketopentanoate (3-ketovalerate), and β-hydroxypentanoate (3-hydroxyvalerate) but without limitation thereto) (Kinman 2006, Am J Physiol Endocrinol Metab 291 (4): E860-6, Brunengraber and Roe 2006, J Inherit Metabol Dis 29 (2-3): 327-31). The examples of precursors of propionyl-CoA described above include the compounds themselves, as well as their salts, prodrugs, solvates and derivatives if applicable.

In some embodiments, the at least one precursor of propionyl-CoA is selected from the group consisting of an uneven chain fatty acid, a triglyceride, a phospholipid and combinations thereof.

The at least one precursor of propionyl-CoA may be an uneven-chain fatty acid, such as a seven-carbon fatty acid. In other embodiments, the at least one precursor of propionyl-CoA is a triglyceride, such as a triglyceride of an uneven chain fatty acid. In further embodiments, the at least one precursor of propionyl-CoA is a phospholipid comprising one or two uneven chain fatty acid(s). In some embodiments, the at least one precursor of propionyl-CoA is a C5 ketone bodies.

Examples of prodrugs include esters, oligomers of hydroxyalkanoate such as oligo(3-hydroxyvalerate) (Seebach 1999, Int J Biol Macromol 25 (1-3): 217-36) and other pharmaceutically acceptable derivatives, which, upon administration to a individual, are capable of providing propionyl-CoA. A solvate refers to a complex formed between a precursor of propionyl-CoA described above and a pharmaceutically acceptable solvent. Examples of pharmaceutically acceptable solvents include water, ethanol, isopropanol, ethyl acetate, acetic acid, and ethanolamine. As used herein, "derivative" compounds of the present invention have been altered, for example by conjugation or complexing with other chemical moieties.

In certain embodiments, the precursor of propionyl-CoA is an uneven chain fatty acid. The invention also includes within its scope esters of uneven chain fatty acids. It will be appreciated by a person of skill in the art that an uneven chain fatty acid may also be referred to as an odd-carbon number fatty acid. The uneven chain fatty acid may be selected from the group consisting of propionic acid, pentanoic acid, heptanoic acid, nonanoic acid and undecanoic acid.

Substituted, unsaturated and/or branched uneven chain fatty acids, as well as other modified uneven chain fatty acids can be used without departing from the scope of the invention.

In other embodiments, the at least one precursor of propionyl-CoA may be one or more compounds of Formula I:

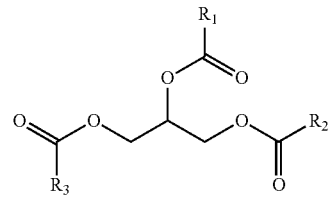

Formula I wherein $R_1$, $R_2$ and $R_3$ are independently selected from alkyl, alkenyl or alkynyl.

In one embodiment, $R_1$, $R_2$ and $R_3$ are independently selected from $C_1$ to $C_{20}$ alkyl, alkenyl or alkynyl.

In a further embodiment, $R_1$, $R_2$ and $R_3$ are independently selected from $C_3$ to $C_{15}$ alkyl, alkenyl or alkynyl.

In another further embodiment, $R_1$, $R_2$ and $R_3$ are independently selected from $C_5$ to $C_{12}$ alkyl, alkenyl or alkynyl.

In yet another further embodiment, $R_1$, $R_2$ and $R_3$ are independently selected from $C_5$ to $C_9$ alkyl, alkenyl or alkynyl.

In certain embodiments, $R_1$, $R_2$ and $R_3$ are the same and are selected from the group consisting of $C_5$, $C_6$, $C_7$, $C_8$ and $C_9$ alkyl, and in particular embodiments, selected from $C_5$, $C_7$ and $C_9$ alkyl and yet in another particular embodiment, $C_7$ alkyl.

In some embodiments, $R_1$, $R_2$ and $R_3$ are independently selected from methyl, ethyl, propyl, butyl, pentyl, hexyl, heptyl, octyl, nonyl, decyl, undecyl, dodecyl, tridecyl, tetradecyl and pentadecyl, inclusive of all isomers.

$R_1$, $R_2$ and $R_3$ may also be independently selected from hexyl, heptyl, octyl and nonyl, inclusive of all isomers.

In particular embodiments, the compound of Formula I is an odd-numbered triglyceride. In certain embodiments, the odd-numbered triglyceride is selected from tripentanoin, triheptanoin and trinonanoin.

In one embodiment, the compound of Formula I is a C7 triglyceride wherein it may contain one, two or three C7 chains.

In one embodiment, the compound of Formula I is triheptanoin, shown below.

This compound may be known by a number of alternative names including 1,3-di(heptanoyloxy)propan-2-yl heptanoate, 1,2,3-propanetriyl triheptanoate and glycerol triheptanoate.

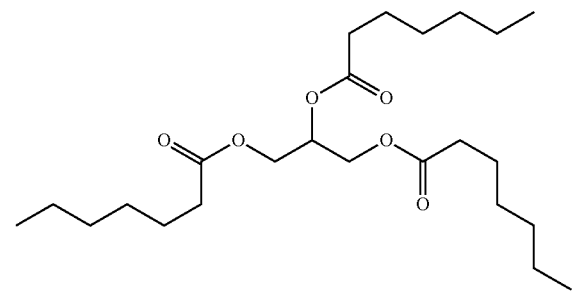

Triheptanoin

In other embodiments, the compound of Formula I is trinonanoin. This compound may be known by a number of alternative names including glyceroltrinonanoate and glyceryltripelargonate.

The term "alkyl" refers to optionally substituted linear and branched hydrocarbon groups having 1 to 20 carbon atoms. Where appropriate, the alkyl group may have a specified number of carbon atoms, for example, $C_1$-$C_6$ alkyl which includes alkyl groups having 1, 2, 3, 4, 5 or 6 carbon atoms in linear or branched arrangements. Non-limiting examples of alkyl groups include methyl, ethyl, propyl, isopropyl, butyl, s- and t-butyl, pentyl, 2-methylbutyl, 3-methylbutyl, hexyl, heptyl, 2-methylpentyl, 3-methylpentyl, 4-methylpentyl, 2-ethylbutyl, 3-ethylbutyl, octyl, nonyl, decyl, undecyl, dodecyl, tridecyl, tetradecyl, pentadecyl.

The term "alkylene" refers to a saturated aliphatic chain substituted at either end, also known as an alkanediyl. Non-limiting examples may include —$CH_2$—, —$CH_2CH_2$— and —$CH_2CH_2CH_2$—.

The term "alkenyl" refers to optionally substituted unsaturated linear or branched hydrocarbon groups, having 2 to 20 carbon atoms and having at least one carbon-carbon double bond. Where appropriate, the alkenyl group may have a specified number of carbon atoms, for example, $C_2$-$C_6$ alkenyl which includes alkenyl groups having 2, 3, 4, 5 or 6 carbon atoms in linear or branched arrangements. Non-limiting examples of alkenyl groups include, ethenyl, propenyl, isopropenyl, butenyl, s- and t-butenyl, pentenyl, hexenyl, hept-1,3-diene, hex-1,3-diene, non-1,3,5-triene and the like.

The term "alkynyl" refers to optionally substituted unsaturated linear or branched hydrocarbon groups, having 2 to 20 carbon atoms and having at least one carbon-carbon triple bond. Where appropriate, the alkynyl group may have a specified number of carbon atoms, for example, $C_2$-$C_6$ alkynyl groups have 2, 3, 4, 5 or 6 carbon atoms in linear or branched arrangements. Non-limiting examples of alkynyl groups include ethynyl, propynyl, butynyl, penrynyl, hexynyl and the like.

In other embodiments, the invention contemplates administration of a phospholipid comprising one or two uneven chain fatty acid(s). The phospholipid may be selected from the group consisting of phosphatidic acid (phosphatidate), phosphatidylethanolamine (cephalin), phosphatidylcholine (lecithin), phosphatidylserine and phosphoinositides.

The person skilled in the art is aware of standard methods for production of precursors of propionyl-CoA. A person skilled in the art is able to determine suitable conditions for obtaining the compounds as described herein, for example, by reference to texts relating to synthetic methodology, non-limiting examples of which are Smith M. B. and March J., March's Advanced Organic Chemistry, Fifth Edition, John Wiley & Sons Inc., 2001 and Larock R. C., Comprehensive Organic Transformations, VCH Publishers Ltd., 1989. Furthermore, selective manipulations of functional groups may require protection of other functional groups. Suitable protecting groups to prevent unwanted side reactions are provided in Green and Wuts, Protective Groups in Organic Synthesis, John Wiley & Sons Inc., 3rd Edition, 1999.

In some embodiments of the invention, the precursor of propionyl-CoA is a seven carbon (C7) fatty acid source or a derivative thereof. Examples of such seven carbon fatty acid source or derivatives thereof include, but are not limited to, triheptanoin, n-heptanoic acid, n-heptanoate, a triglyceride comprising n-heptanoic acid or comprising n-heptanoic acid and a different fatty acid such as n-pentanoic acid, n-nonanoic acid, or both. Examples of derivatives of seven carbon fatty acid source also include, but are not limited to, 4-methylhexanoate, 4-methylhexenoate, 3-hydroxy-4-methylhexanoate, 5-methylhexanoate, 5-methylhexenoate and 3-hydroxy-5-methylhexanoate.

For example, one embodiment of a seven carbon fatty acid source is triheptanoin, which is a triglyceride that can be made by the esterification of three n-heptanoic acid molecules and glycerol by any means known in the art. Triheptanoin is also commercially available through Ultragenyx Pharmaceutical, although without limitation thereto.

Another example of seven-carbon fatty acid is n-heptanoic acid. n-Heptanoic acid is a saturated straight chain seven-carbon fatty acid with the following structure:

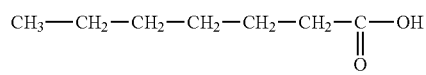

Heptanoic acid is found in various fusel oils in appreciable amounts and can be extracted by any means known in the art. It can also be synthesized by oxidation of heptaldehyde with potassium permanganate in dilute sulfuric acid (Ruhoff, Org Syn Coll. voIII, 315 (1943)). Heptanoic acid is also commercially available through Sigma Chemical Co. (St. Louis, Mo.).

According to the present invention, any seven carbon fatty acid source or derivatives thereof can be used for the treatment methods provided in the present invention. The terms heptanoic acid, heptanoate, and triheptanoin may be used interchangeably in the present description. It will be understood by those skilled in the art that heptanoic acid, heptanoate, and triheptanoin are used throughout the present description as an exemplary seven-carbon fatty acid source to be used in the invention and is intended to be illustrative of the invention, but is not to be construed to limit the scope of the invention in any way. Substituted, unsaturated, or branched heptanoate, as well as other modified seven-carbon fatty acid source can be used without departing from the scope of the invention.

In some embodiments, the C7 fatty acid source is provided in a formulation that has minimum impurity, e.g., the formulation contains at least 90%, 91%, 92%, 93%, 94%, 95%, 96%, 97%, 98%, or 99% triheptanoin. In some other embodiments, the C7 fatty acid source has an acid value has an acid value of 0.1 or less mg KOH/gr, a hydroxyl value of 2.8 or less mg KOH/gr.

According to the present invention, the precursors of propionyl-CoA may be used as single agents or in association with other therapeutic agents or treatments. In some embodiments, they are used in combination with other therapeutic agents. For example, a precursor of propionyl-CoA may be used in combination with a carnitine supplement, biotin, vitamin B12, or combinations thereof. An example of carnitine supplement is L-carnitine. An example of vitamin B12 is Cyanocobalamin.

By "administration" or "administering" is meant the introduction of a composition (e.g., a composition comprising one or more anaplerotic agents) into a subject by a chosen route.

The term "therapeutically effective amount" describes a quantity of a specified agent sufficient to achieve a desired effect in a subject being treated with that agent. For example, this can be the amount of a composition comprising one or more anaplerotic agents necessary to reduce, alleviate, prevent and/or delay the onset of one or a plurality of symptoms of a neurodegenerative and/or neuromuscular disease, disorder or condition. In some embodiments, a "therapeutically effective amount" is sufficient to reduce or eliminate a symptom of a neurodegenerative and/or neuromuscular disease, disorder or condition. In other embodiments, a "therapeutically effective amount" is an amount sufficient to achieve a desired biological effect, for example an amount that is effective to reverse, at least in part, the impaired mitochondrial function associated with a neurodegenerative and/or neuromuscular disease, disorder or condition.

Ideally, a therapeutically effective amount of an anaplerotic agent is an amount sufficient to induce the desired result without causing a substantial cytotoxic effect in the subject. The effective amount of an anaplerotic agent useful for reducing, alleviating, preventing and/or delaying the onset of one or more symptoms of a neurodegenerative and/or neuromuscular disease, disorder or condition will be dependent on the subject being treated, the type and severity of any associated disease, disorder and/or condition, and the manner of administration of the therapeutic composition.

The present invention includes within its scope a therapeutic amount of one or more anaplerotic agents that are less than 100% of dietary caloric intake and may be within a range from between about 5% and about 90%, between about 15% and about 80%, between about 20% and about 60%, between about 25% and 50% and/or between about 30% and about 40%.

In particular embodiments, the one or more anaplerotic agents are provided to the animal in an amount comprising at least about 5%, at least about 10%, at least about 15%, at least about 20%, at least about 20.5%, at least about 21%, at least about 21.5%, at least about 22%, at least about 22.5%, at least about 23%, at least about 23.5%, at least about 24%, at least about 24.5% at least about 25%, at least about 25.5%, at least about 26%, at least about 26.5%, at least about 27%, at least about 27.5%, at least about 28%, at least about 28.5%, at least about 29%, at least about 29.5%, at least about 30%, at least about 30.5%, at least about 31%, at least about 31.5%, at least about 32%, at least about 32.5%, at least about 33%, at least about 33.5%, at least about 34%, at least about 34.5%, at least about 35%, at least about 35.5%, at least about 36%, at least about 36.5%, at least about 37%, at least about 37.5%, at least about 38%, at least about 38.5%, at least about 39%, at least about 39.5%, at least about 40%, at least about 40.5%, at least about 41%, at least about 41.5%, at least about 42%, at least about 42.5%, at least about 43%, at least about 43.5%, at least about 44%, at least about 44.5%, at least about 45%, at least about 45.5%, at least about 46%, at least about 46.5%, at least about 47%, at least about 47.5%, at least about 48%, at least about 48.5%, at least about 49%, at least about 49.5%, at least about 50%, at least about 55%, at least about 60%, about at least about 70%, at least about 80%, at least about 90% or more of the dietary caloric intake.

In one embodiment, the one or more anaplerotic agents are provided to the animal in an amount comprising at least about 5% of the dietary caloric intake for the animal.

In a further embodiment, the one or more anaplerotic agents are provided to the animal in an amount comprising at least about 20% of the dietary caloric intake for the animal.

In another further embodiment, the one or more anaplerotic agents are provided to the animal in an amount comprising at least about 30% of the dietary caloric intake for the animal.

In yet another further embodiment, the one or more anaplerotic agents are provided to the animal in an amount comprising at least about 35% of the dietary caloric intake for the animal.

It will be appreciated by a skilled addressee that "% of dietary caloric intake" may relate to % of kJoules or % of kcal.

Any safe route of administration may be employed for providing a patient with the one or more anaplerotic agents. For example, enteral, oral, rectal, parenteral, sublingual, buccal, intra-duodenal, intra-gastric, intravenous, intra-articular, intra-muscular, intra-dermal, subcutaneous, inhalational, intraocular, intraperitoneal, intracerebroventricular, transdermal and the like may be employed. It can be administered via ingestion of a food substance containing triheptanoin at a concentration effective to achieve therapeutic levels. Alternatively, it can be administered as a capsule or entrapped in liposomes, in solution or suspension, alone or in combination with other nutrients, additional sweetening and/or flavoring agents. Capsules and tablets can be coated with shellac and other enteric agents as is known.

Dosage forms include tablets, dispersions, suspensions, injections, solutions, syrups, oils troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Anaplerotic agents for enteral, intraperitoneal, oral or parenteral administration may be presented in discrete units such as capsules, sachets or tablets each containing a predetermined amount of the therapeutic agent of the invention, as a powder or granules or as a solution or a suspension in an aqueous liquid, a non-aqueous liquid, an oil-in-water emulsion or a water-in-oil liquid emulsion. In certain embodiments, administration of the one or more anaplerotic agents is by way of oral administration. Such therapeutically effective amounts of the one or more anaplerotic agents may be prepared by any of the methods of pharmacy but all methods include the step of bringing into association one or more agents as described above with the carrier which constitutes one or more necessary ingredients. In general, such compositions may be prepared by uniformly and intimately admixing the agents of the invention with liquid carriers or finely divided solid carriers or both, and then, if necessary, shaping the product into the desired presentation.

The anaplerotic agents may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

It will also be appreciated that treatment methods may be applicable to prophylactic or therapeutic treatment of mammals, inclusive of humans and non-human mammals such as livestock (e.g. horses, cattle and sheep), companion animals (e.g. dogs and cats), laboratory animals (e.g. mice rats and guinea pigs) and performance animals (e.g. racehorses, greyhounds and camels), although without limitation thereto.

In a further aspect, the invention provides a kit for the treatment of an animal with a neurodegenerative and/or neuromuscular disease, disorder or condition comprising: (i) a therapeutically effective amount of one or more anaplerotic agents described herein; and (ii) instructions for use.

The one or more anaplerotic agents may be selected from tripentanoin, triheptanoin and trinonanoin.

In a particular embodiment, the one or more anaplerotic agents is triheptanoin.

The one or more anaplerotic agents of this aspect may further comprise a pharmaceutically-acceptable carrier, diluent or excipient. Such a pharmaceutically-acceptable carrier, diluent or excipient may include a solid or liquid filler, diluent or encapsulating substance that may be safely used in systemic administration. A useful reference describing pharmaceutically acceptable carriers, diluents and excipients is Remington's Pharmaceutical Sciences (Mack Publishing Co. N.J. USA, 1991) which is incorporated herein by reference.

It would be appreciated that certain embodiments of this aspect may further comprise one or more additional therapies for a neurodegenerative and/or neuromuscular disease, disorder and/or condition. These may include, for example, antioxidants, anti-inflammatories, anti-apoptotic compounds, cholinesterase inhibitors, acetylcholine receptor agonists and/or antagonists, α-adrenoceptor agonists and/or antagonists, monoamine oxidase inhibitors, catechol-O-methyl transferase inhibitors, nitric oxide donors, analgesics, riluzole (Rilutek®), muscle relaxants and/or anticonvulsants, albeit without limitation thereto.

The one or more anaplerotic agents of this aspect may comprise a dosage form as described hereinbefore. Furthermore, a skilled artisan would readily acknowledge that certain embodiments of the present aspect may include devices suitable for dispensing the dosage form/s and/or composition/s of said kit. Such dispensing devices may include, for example, one or more of a syringe and/or needle, blister pack, applicator, cup or suitably shaped container, inhalant device, spoon, dropper, nebulizer, transdermal patch, gauze and/or bandage, albeit without limitation thereto.

In another further aspect, the invention provides a method of determining whether an animal has, or is predisposed to, a neurodegenerative and/or neuromuscular disease, disorder or condition, wherein the method includes the step of measuring (i) the expression level of one or more nucleic acids that respectively encode enzymes associated with energy metabolism (ii) the expression level and/or activity of said enzymes and/or (iii) the level of one or more metabolites associated with energy metabolism.

In yet another further aspect, the invention provides a method of monitoring the response of an animal to treatment or prevention of a neurodegenerative and/or neuromuscular disease, disorder or condition by administration of one or more anaplerotic agents, wherein the method includes the step of measuring (i) the expression level of one or more nucleic acids that respectively encode enzymes associated with energy metabolism (ii) the expression level and/or activity of said enzymes and/or (iii) the level of one or more metabolites associated with energy metabolism.

The neurodegenerative and/or neuromuscular disease, disorder or condition is as hereinbefore described.

By "energy metabolism" is meant the sum total of all the chemical reactions and/or processes involved in maintaining the energy supply of a cell and thus an organism. These reactions and/or processes are largely catalyzed by enzymes, and typically involve the breakdown of larger molecules, such as carbohydrates like glucose, to smaller molecules to extract energy. For the present invention, those substances involved in or produced as a result of these reactions and/or processes are referred to as metabolites. Broadly, energy metabolism includes, but is not limited to, glycolysis, the TCA cycle, oxidative phosphorylation, anaplerosis and anaerobic respiration.

In some embodiments of the methods of the invention, the enzymes or metabolites may be selected from the group consisting of glycolytic enzymes or metabolites, TCA cycle enzymes or metabolites and anaplerotic enzymes or metabolites.

Non-limiting examples of glycolytic enzymes include hexokinase, phosphoglucose isomerase, phosphofructokinase, fructose-biphosphate aldolase, triose-phosphate isomerase, glyceraldehyde phosphate dehydrogenase, phosphoglycerate kinase, phosphoglycerate mutase, enolase, pyruvate kinase, pyruvate dehydrogenase, dihydrolipoyl transacetylase and dihydrolipoyl dehydrogenase.

In specific embodiments, the glycolytic enzyme is pyruvate dehydrogenase alpha 1, phosphoglucose isomerase (PGI), or phosphofructokinase (PFK).

Non-limiting examples of glycolytic metabolites include glucose, glucose 6-phosphate, fructose 6-phosphate, fructose 1,6-biphosphate, glyceraldehyde 3-phosphate, 1,3-biphosphoglycerate, 3-phosphoglycerate, 2-phosphoglycerate, phosphoenolpyruvate, pyruvate and lactate.

Non-limiting examples of TCA cycle enzymes include citrate synthase, aconitase, isocitrate dehydrogenase, oxoglutarate dehydrogenase, succinyl-CoA synthetase, succinate dehydrgoenase complex, fumarase, Complex I (a.k.a. NADH dehydrogenase or NADH ubiquinone oxidoreductase), and malate dehydrogenase.

The TCA cycle enzymes may be selected from the group consisting of oxoglutarate dehydrogenase and succinate dehydrogenase complex subunit A.

Non-limiting examples of TCA cycle metabolites include acetyl CoA, citrate, cis-Aconitate, isocitrate, oxalosuccinate, oxoglutarate, succinyl CoA, succinate, fumurate, malate and oxaloacetate.

Non-limiting examples of anaplerotic enzymes include pyruvate carboxylase, aspartate transaminase, glutamate dehydrogenase, methylmalonyl-CoA mutase, adenylosuccinate lyase, glutamate pyruvate transaminase 1, glutamate pyruvate transaminase 2 and propionyl-CoA carboxylase subunits A and B.

The anaplerotic enzymes may be selected from the group consisting of glutamate-pyruvate transaminase 1, glutamate-pyruvate transaminase 2, propionyl-CoA carboxylase subunit A and B and methylmalonyl-CoA mutase.

Non-limiting examples of anaplerotic metabolites include aspartate, alanine, GABA, citrate, succinate, malate, fumarate, alpha-ketoglutarate (2-oxo-glutarate), glutamate, glutamine, proline, histidine, arginine, phenylalanine, tyrosine, methionine, isoleucine, valine, propionyl CoA, methylmalonyl CoA and adenylosuccinate.

A person skilled in the relevant art would readily acknowledge that if the levels of metabolites associated with the TCA cycle and/or anaplerosis, such as lactate, alanine, pyruvate, aspartate, glutamate, glutamine and aspartate, are lowered, this indicates that there may be less TCA cycle intermediates and/or less anaplerosis.

As would be well appreciated by the skilled artisan, reference herein to an increased or decreased level of expression (e.g a nucleic acid or protein expression level, or the level of a metabolite) or activity (e.g enzyme activity) includes and encompasses relative and absolute levels of expression. By way of example, a relative level of expression or activity may be determined relative to a reference or standard level of expression or activity, such as in a sample obtained from a normal or non-suffering individual or population of individuals.

A change or alteration in the level of a metabolite or the level of a enzyme's protein expression, gene expression and/or enzymatic activity in an animal that has, or is predisposed to, a neurodegenerative and/or neuromuscular disease, disorder or condition may be determined by comparing such levels from a biological sample obtained from said animal to either those levels of another animal known not to have, nor be predisposed to, a neurodegenerative and/or neuromuscular disease, disorder or condition or those levels of the general population or a reference population.

In one embodiment, a decrease or reduction in the expression level of one or more nucleic acids that respectively encode enzymes associated with energy metabolism and/or a decrease or reduction in the expression level and/or activity of said enzyme(s) and/or a decrease or reduction in the level of one or more metabolites associated with energy metabolism indicate that said animal has, or is predisposed to, the neurodegenerative and/or neuromuscular disease, disorder or condition.

In yet another embodiment an increase in the expression level of one or more nucleic acids that respectively encode enzymes associated with energy metabolism and/or an increase in the expression level and/or activity of said enzyme(s) and/or an increase in the level of one or more metabolites associated with energy metabolism indicate that said animal is responding to the administration of one or more anaplerotic agents.

Typically, the one or more nucleic acids that respectively encode enzymes associated with energy metabolism and/or said enzyme(s) and/or the one or more metabolites associated with energy metabolism are detected or measured in a biological sample. The sample may be a fluid, cell or tissue sample obtained from the animal.

In this context, a "nucleic acid" may be single- or double-stranded DNA inclusive of genomic DNA and cDNA although without limitation thereto or may be single- or double-stranded RNA inclusive of mRNA and miRNA, although without limitation thereto. A particular example of a nucleic acid is an "amplification product" resulting from nucleic acid sequence amplification. Non-limiting examples of primers suitable for nucleic acid amplification of nucleic acids encoding these enzymes comprise respective nucleotide sequences set forth in Table 1.

TABLE 1

Gene names, GenBank accession numbers, symbols, forward and reverse primer sequences (SEQ ID NOS: 1-20) used for the gene expression studies of metabolic genes.

| Gene | Symbol | Sequence 5' to 3' |
| --- | --- | --- |
| Propionyl-CoA Carboxylase (Subunit A) NM_144844.2 | Pcca | F AGAATTGCAAGGGAAATTGG (SEQ ID NO: 1) R CTAAAGCCATCCCTGGTCTC (SEQ ID NO: 2) |
| Propionyl-CoA Carboxylase (Subunit B) NM_025835.2 | Pccb | F AGCCTACAACATGCTGGACA (SEQ ID NO: 3) R GGTCCTCCCATTCATTCTTG (SEQ ID NO: 4) |
| Methylmalonyl-CoA mutase NM_008650.3 | Mut | F CCAAACACTGACCGTTCTCA (SEQ ID NO: 5) R GGAATGTTTAGCTGCTTCAGG (SEQ ID NO: 6) |
| Pyruvate carboxylase NM_008797.3 | Pcx | F GAGCTTATCCCGAACATCCC (SEQ ID NO: 7) R TCCATACCATTCTCTTTGGCC (SEQ ID NO: 8) |
| Pyruvate dehydrogenase E1 alpha 1 NM_008810.2 | Pdha1 | F AACTTCTATGGAGGCAACGG (SEQ ID NO: 9) R CTGACCCTGATTAGCAGCAC (SEQ ID NO: 10) |
| Glyceraldehyde-3-phosphate dehydrogenase NM_008084.2 | Gapdh | F ATACGGCTACAGCAACAGGG (SEQ ID NO: 11) R TCTTGCTCAGTGTCCTTGCT (SEQ ID NO: 12) |
| Oxoglutarate dehydrogenase NM_010956.4 | Ogdh | F TGCAGATGTGCAATGATGAC (SEQ ID NO: 13) R GCAGCACATGGAAGAAGTTG (SEQ ID NO: 14) |
| Succinate dehydrogenase complex (Subunit A) NM_023281.1 | Sdha | F GGAACACTCCAAAAACAGACCT (SEQ ID NO: 15) R CCACCACTGGGTATTGAGTAGAA (SEQ ID NO: 16) |

TABLE 1-continued

Gene names, GenBank accession numbers, symbols, forward and reverse primer sequences (SEQ ID NOS: 1-20) used for the gene expression studies of metabolic genes.

| Gene | Symbol | Sequence 5' to 3' |
|---|---|---|
| Glutamate-pyruvate transaminase 1 NM_182805.2 | Gpt1 | F TGAGGTTATCCGTGCCAATA (SEQ ID NO: 17) R GTCCGGACTGCTCAGAAGAT (SEQ ID NO: 18) |
| Glutamate-pyruvate transaminase 2 (alanine aminotransferase) NM_173866.3 | Gpt2 | F GCGACGGTATTTCTACAATCC (SEQ ID NO: 19) R CGCGGAGTACAAGGGATACT (SEQ ID NO: 20) |

As are well known in the art, methods of measuring gene expression may include, but are not limited to, northern blotting, nucleic acid amplification techniques (e.g. qPCR, real-time PCR and competitive PCR), high throughput expression profiling (e.g. microarrays), serial analysis of gene expression (SAGE) and RNA-seq.

Suitable techniques at measuring the expression level of enzymes associated with energy metabolism are similarly well known. Such techniques may include, but are not limited to, immunoassays, (e.g. western blots), radioimmunoassays, enzyme-linked immunosorbent assays (ELISAs), protein microarray techniques (e.g. reverse phase protein microarray (RPPA), histological methods (e.g. immunofluorescence (IF) and immunohistochemistry (IHC)), colorimetric/fluorometric/luminescence assays and proteomics approaches such as mass spectrometry (MS) and high-performance liquid chromatography (HPLC).

Suitable techniques for measuring the level of metabolites associated with energy metabolism are also well known in the art. Such techniques may include, but are not limited to colorimetric/fluorometric/luminescence enzymatic assays, high-performance liquid chromatography (HPLC), mass spectrometry (MS) coupled with gas or liquid chromatography (GC-MS or LC-MS) and histological methods (e.g. immunofluorescence (IF) and immunohistochemistry (IHC) for GABA).

The person skilled in the art would be well aware of standard methods for measuring enzymatic activity, such as those described in Enzyme Assays: A Practical Approach (The Practical Approach Series) by Eisenthal R and Danson M ($2^{nd}$ edition, Oxford University Press, 2002) which is incorporated by reference herein.

So that the invention may be readily understood and put into practical effect, the following non-limiting Example is provided.

EXAMPLES

Example 1—Effects of Triheptanoin on ALS in an Animal Model

Materials and Methods

Animals

All experiments were approved by the University of Queensland's Animal Ethics Committee and followed the guidelines of the Queensland Animal Care and Protection Act 2001. All efforts were made to minimize the suffering and the number of animals used. Wild-type and hSOD1$^{G93A}$ mice (B6.Cg-Tg(SOD1*G93A)1 Gur/J, stock no. 004435, Jackson laboratory, Maine, USA), were generated by mating hSOD1$^{G93A}$ males with C57B/L6 wild-type females (University of Queensland). Mice were housed in a 12 hour light, 12 hour dark cycle, and had free access to food and water. Experimenters were blinded to animal genotype (until the mice started expressing the ALS phenotype) and dietary interventions.

Dietary Intervention

Immediately after weaning, mice were placed on either a standard diet (SF11-027, Specialty Feeds, WA, AUS) or a matched diet (SF11-028, Specialty Feeds) in which 35% of the calories were from triheptanoin oil (Sasol, Germany). All diets were matched in protein, mineral, antioxidant and vitamin content relative to their caloric densities (Thomas et al., 2012). Triheptanoin replaced sucrose, some of the complex carbohydrates and long chain fats in the diet.

Enzyme Assays

The cytosolic and mitochondrial fractions were isolated from the gastrocnemius muscle via homogenisation (Potter-Elvehjem tissue grinder) in cold isolation buffer (10 mM EDTA, 215 mM D-mannitol, 75 mM sucrose, 0.1% BSA and 20 mM HEPES, pH 7.4). Samples were centrifuged at 700 g for 10 minutes at 4° C. The supernatant was collected and centrifuged at 10,500 g for 10 minutes at 4° C., the supernatant collected, and the pellet resuspended in 1 mL isolation buffer. The centrifugation process was repeated, and the collective supernatant (cytosolic fraction) and resuspended pellet (mitochondrial fraction) stored at −80° C.

The activities of all enzymes were measured by continuous spectrophotometric assays at 25° C. on Sunrise Tecan microplate reader (Tecan, Mannedorf Switzerland). The reduction of NAD and NADP (OGDH and PGI activity, respectively) or the oxidation of NADH (PFK activity) was measured by the change in absorbance over time at a wavelength of 340 nm. All activity rates were corrected to milligrams of protein in samples, using the BCA protein Assay kit (Thermo Scientific, Illinois, USA).

OGDH Assay

The assay was adapted from Lai & Cooper, 1986. The assay mixture contained 50 mM Tris-HCl (pH 7.4), 0.2 mM sodium CoA, 2 mM Nicotinamide adenine dinucleotide, 0.5 mM, thiamine pyrophosphate, 0.5 mM magnesium chloride, 10 mM dithiothreitol and 10 µL of isolated mitochondria from sample. Reactions were initiated by the addition of 10 mM oxoglutarate to measure the reduction of NAD.

PGI Assay

The activity of phosphoglucose isomerase (PGI) was measured by coupling the reaction to NADP reduction via glucose 6-phosphate dehydrogenase. The assay mixture contained 100 mM Tris-HCl (pH 7.4), 0.6 mM nicotinamide adenine dinucleotide phosphate, 17.5 mM magnesium chloride, 5 U/mL glucose 6-phosphate dehydrogenase (G8404, Sigma Aldrich), and 5 µL of the cytosolic fraction from samples. The reaction was initiated by the addition of 10 mM fructose 6-phosphate.

PFK Assay

The activity of phosphofructokinase was measured by coupling the production of fructose 1,6-bisphosphate from the reaction to the enzymes aldolase, α-glycerophosphate dehydrogenase and triosephosphate isomerase to measure the oxidation of NADH. The assay mixture contained 80 mM Tris-HCl (pH 7.4), 2 mM dithiothreitol, 3.6 mM adenosine triphosphate, 0.6 mM nicotinamide adenine dinucleotide reduced, 20 mM magnesium chloride, 6 U/mL aldolase (A8811, Sigma Aldrich), 1 U/mL α-glycerophosphate dehydrogenase and 5 U/mL triosephosphate isomerase (G1881, Sigma Aldrich) and 5 µL of the cytosolic fraction from samples. The reaction was initiated by the addition of 15 mM fructose 6-phosphate.

Behavioral Testing and Observation

Animals underwent behavioral testing approximately 3-4 hours into the light cycle. All behavioral testing was conducted in an environment with minimal stimuli so as to minimize any possible effects caused by changes in external stimuli. Animals were weighed before every test session. Mice were observed, and disease progression tracked and graded according to a neurological score sheet to ensure that any non-ALS related deaths were excluded from the study. The neurological score was adapted from criteria developed at the ALS therapy development institute (Gill et al., 2009). In accordance with ethical requirements, hSOD1$^{G93A}$ mice that became too weak to reach the food hoppers were provided with wet chow on the floor of the cages. The endpoint of the study was defined as the mouse being unable to right itself within 15 seconds after being placed on its back. Upon reaching end-stage or 25 weeks of age, transgenic mice and their respective wild-type littermates were euthanized with an overdose of pentobarbital (120 mg/kg, i.p., Provet, Australia). Tissues, including the m. gastrocnemius and tail, were collected for subsequent analysis. To measure the time point when body weight loss started, we defined the day where a loss of more than 10% of the combined mean body weight from week 12 to 17 was observed and all subsequent three measurements were ≤90% of the original mean weight.

Hind Limb Grip Strength Test

Hind limb grip strength tests were conducted twice a week using a T-bar force transducer (Ugo Basile, Italy). The animal was held by the tail, ensuring its hind limbs were gripping the T-bar before being pulled downwards at a 60° angle. The reading on the force transducer was taken only if both hind limbs released the bar at the same time. The average of 10 trials per mouse was recorded each training session. To compare time points of grip strength loss, the time point where a loss of more than 30% of the combined mean grip strength of week 9 to 13 was recorded, if the subsequent 3 measurements were ≤70% of the original average strength.

Rotarod Test

The rotarod tests were conducted with 10 repeats once a week using a rotarod designed for mice (Ugo Basile, Italy). Animals were placed on the rod and the rod was then rotated for 3 min at 25 revolutions per min. The time at which the animal fell off was recorded. We defined the age of balance loss on the rotarod when this time was zero.

Quantitative Genotyping

All mice were genotyped post-mortem by real time quantitative PCR according to a previously described procedure to assess relative copy number of the hSOD1$^{G93}$A transgene (Alexander et al., 2004). Primers used were documented by the Jackson laboratory for genotyping with conventional PCR (http://jaxmice.jax.org). The final concentration of forward and reverse primers in each reaction was 0.4 µM for hSOD and 0.5 µM for mouse interleukin 2 (mIl2) mixed with 5 ng genomic DNA and 5 µl of SYBR Green Mastermix (Applied Biosystems, CA, USA) The thermal profile for the assay was an initial hot start of 95° C. for 10 minutes, followed by 40 cycles of 95° C. for 30 seconds, 60° C. for 1 minute and 72° C. for 30 seconds (ABI 7900HT Fast Real-Time PCR system, Applied Biosystems). Lastly the melt curve was generated by heating to 95° C. for 2 minutes, cooling to 60° C. for 15 seconds and a final 2% heating ramp to 95° C. for 15 seconds. Water was added to replace the DNA in the negative controls. CT values were calculated by the Sequence Detection Software 2.4 from the raw data. Copy number was then calculated using the equation documented below.

$$\text{Copy number} = (2^{(CT_{hSOD1}Log_2 1.82) - (CT_{mIl2}Log_2 2.01)})2$$

RNA Extraction, cDNA Synthesis, Quantitative Real Time PCR Assay.

After euthanasia, the gastrocnemius muscle was quickly removed and frozen in liquid nitrogen. To extract RNA, muscle samples were pulverized in liquid nitrogen with a cold mortar and pestle, dissolved with TRI reagent (Life Technologies, CA, USA) and extracted according to the manufacturer's instructions. Contaminating DNA was removed by DNase I treatment and cDNA was synthesized using the Tetro cDNA synthesis kit (Bioline, London, UK) according to the manufacturer's instructions.

Expression of several metabolic genes was assayed (Gapdh, Pdha1, Ogdh, Sdha, Pcx, Gpt1, Gpt2, Pcca, Pccb and Mut) by quantitative real time PCR. All primers pairs (Table 1) were evaluated for efficiency using a 4 fold serial dilution series of muscle cDNA. The derived slope of each primer pair was used to calculate the efficiency by applying the formula, $4^{[(-1/slope)-1]*100}$. Reactions consisted with diluted cDNA, 5 µl of SYBR Green Mastermix and 8 µM of forward and reverse primers each, and were amplified after an initial hot start. Conditions for cycling and the melt curve were identical to those described for quantitative genotyping. Samples without reverse transcriptase treatment were assayed to ensure that samples were free from DNA contamination. The fold expression (ΔCT) of the gene of interest (goi) relative to the geometric mean of housekeeping genes (Tbp, B2m and Hmbs) were calculated with a formula adapted from (Vandesompele et al., 2002) taking into consideration the individual efficiencies (E) of each primer pair.

$$\Delta CT_{goi} = 2^{-}[(CT_{goi}Log2E_{goi}) - 3\sqrt{(CT_{TBP}Log_2 2.03)(CT_{B2m}Log_2 2.03)(CT_{HMBS}Log_2 1.86)}]$$

Motor Neuron Counting

Mice were fed with control or triheptanoin diet from 35 days until 70 days of age, when mice were anesthetized with pentobarbital (100 mg/kg i.p.), perfused with 0.9% saline followed by 4% paraformaldehyde. Spinal cords were removed and further fixed in 4% paraformaldehyde and subsequently embedded in OCT compound and serial sections of 16 µm were cut from lumbar vertebrae. Sections were washed in cold PBS and stained with 0.1% thionin in acetate buffer (pH3.4). The motor neurons were counted using stereological method as previously described (Banks et al., 2001; 2003; Forgarty et al., 2013). Briefly, motor neurons in the lateral motor column (LMC) from one side of the spinal cord were counted and only neurons that are large in size with darkly stained cytoplasm, pale nucleus and darkly stained nucleoli were counted (Clarke and Oppenheim, 1995). Every $10^{th}$ section from lumbar 2 to lumbar 5 regions was counted to get the total motor neuron count which was then divided by the number of sections counted and multiplied by the total number of sections containing the LMC.

Data Analysis

Statistics were performed with Graphpad Prism (version 5.03) using one or two-way ANOVA followed by Bonferroni multiple comparisons post-hoc tests for analysis of several groups. For the comparison of the onset of body weight loss and the area under the curve (AUC) for hind limb grip strength, two-tailed unpaired t-tests were employed. Linear regression analysis with comparison of slope and intercept was used to compare age of hind limb grip strength loss and body weight loss vs. transgene copy number. Data are represented as mean±SEM.

Power analysis using the average standard deviations for onsets of loss of grip strength and balance on rotarod showed that n=5 was sufficient to observe changes between means by 2.3 and 1.5 weeks, respectively with 80% power at the 0.05 significance level.

Results

Figure 2:
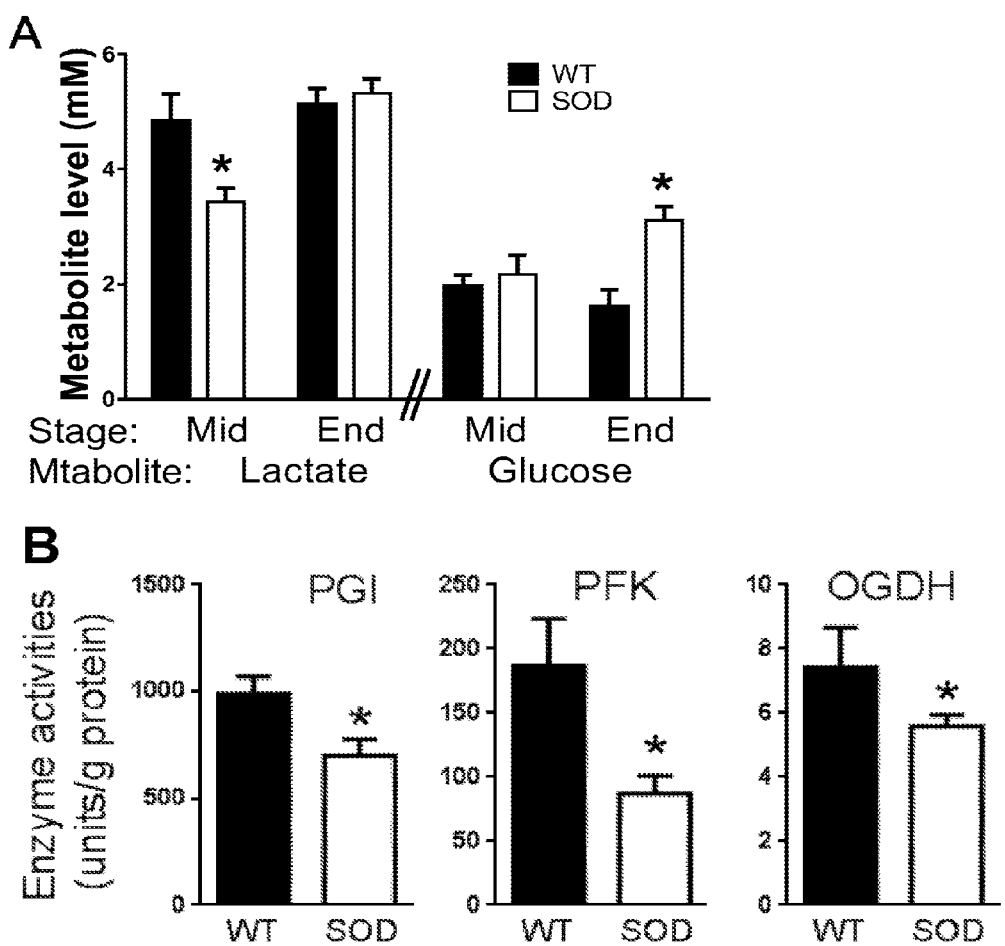
FIG. 2 shows alterations in metabolism in m. gastrocneminus of hSOD1$^{G93A}$ mice at mid and end stage of disease. Panel A depicts the metabolite levels of lactate or glucose in wild-type (WT) or hSOD1$^{G93A}$ (SOD) mice. Lactate levels are decreased at mid stage (110-130 days) in the SOD mice as compared to the WT mice, indicating reduced glycolysis, while there is an increase in glucose at end stage (150-175 days) in the SOD mice as compared to the WT mice, indicating decreased glucose metabolism. Panel B depicts the enzyme activity levels of several enzymes in wild-type (WT) or hSOD1$^{G93A}$ (SOD) mice at mid disease (110-130 days). The data show reduction in maximal enzyme activities in the m. gastrocneminus in the SOD mice as compared to the WT mice. PGI—phosphoglucose isomerase—28.5% decrease, PFK—phosphofructokinase—53% decrease, OGDH—oxoglutarate dehydrogenase—25% decrease. * p<0.05 t-tests. N=5-8 mice/group.

Metabolic alterations in muscle of hSOD1$^{G93A}$ mice. First we set out to confirm that energy metabolism is affected in hSOD1$^{G93A}$ mice at the mid and end disease stage. Specifically, we found that in the m. gatrognenicus, lactate levels are reduced at mid stage (110-130 days) by 29%, indicating reduced glycolysis (FIG. 2, panel A). This was may be explained by the observed reduction in the maximal activity of phosphoglucose isomerase by 28.5% and phosphofructokinase by 53% decrease, while the oxidative stress-sensitive TCA cycle enzyme-oxoglutarate dehydrogenase maximal activity was reduced by 25% (* p<0.05 t-tests. N=5-8 mice/group, FIG. 2, panel B). In contrast at end stage, muscle glucose levels were elevated 1.9-fold, suggesting loss of glycolysis.

Figure 3A:
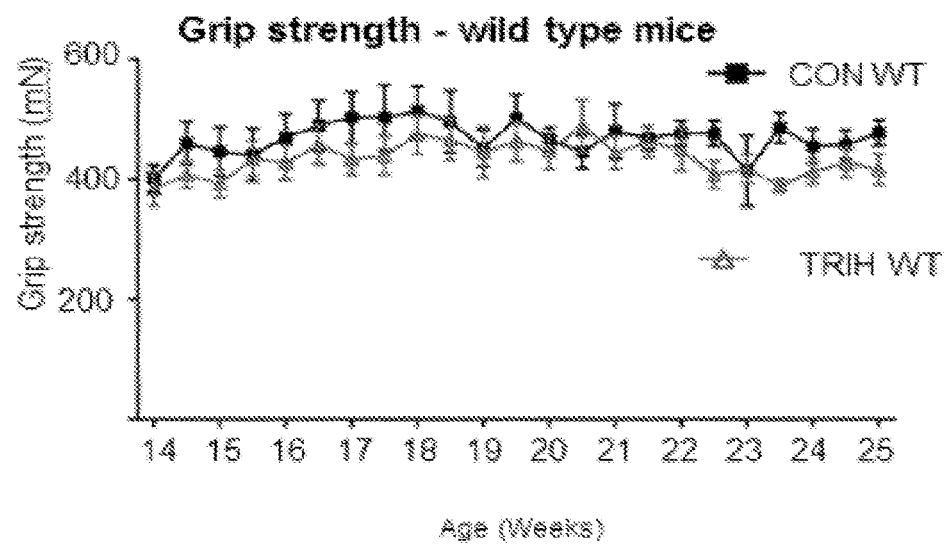
FIGS. 3A-3E show that triheptanoin treatment delays the loss of hind limb grip strength in hSOD1$^{G93A}$ mice.

Triheptanoin delays the onset of loss of hind limb grip strength and balance in hSOD1$^{G93A}$ mice. One of the characteristics of ALS in hSOD1$^{G93A}$ mice is the progressive loss of muscle mass and strength. Thus, hind limb grip strength tests were used to assess the course of disease progression in mice on either a control or triheptanoin diet. There was no observable difference between the mean hind limb grip strength of the wild-type mice on the control diet (n=12) when compared to those on the triheptanoin diet (n=15; all hSOD1$^{G93A}$ mice including lower transgene copy number). Mean hind limb grip strengths for control fed and triheptanoin fed wild-type mice consistently fell between 300 and 600 mN (FIG. 3A).

During the course of the experiments, it was observed that some hSOD1$^{G93A}$ mice developed a loss of hind limb grip strength after 22 weeks of age. Analysis of hSOD1$^{G93A}$ transgene copy number revealed that a subpopulation of hSOD1$^{G93A}$ mice had only 12-17 copies of the SOD1 transgene. Assessing all mice (FIG. 3E), the linear regressions between the age of strength loss beginning against transgene copy numbers are significantly different between the groups fed control diet ($R^2$=0.89) vs. triheptanoin ($R^2$=0.91). Specifically, the x and y intercepts are different between the two regression lines (p<0.001) (indicating that triheptanoin effectively delays onset of grip strength loss), but not the slopes (p=0.90).

Figure 3B:
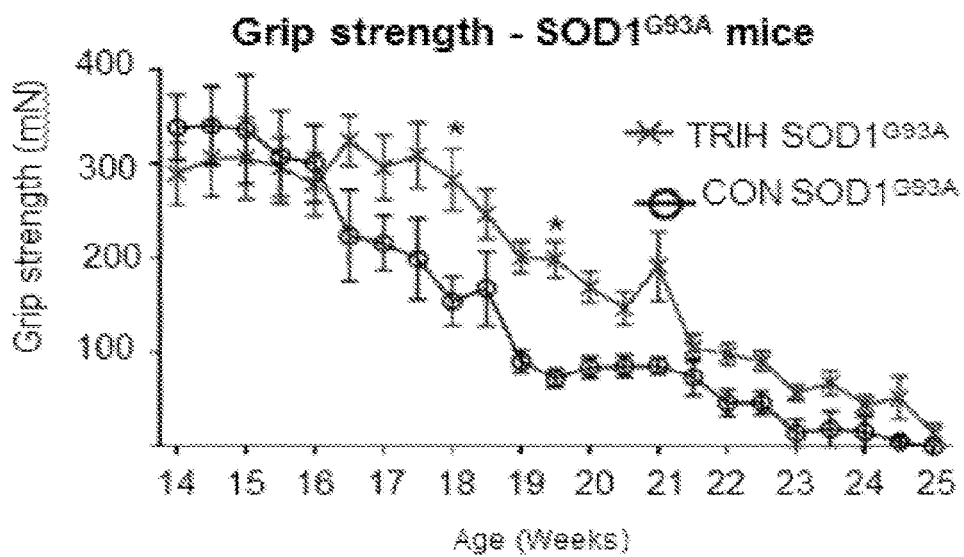
Figure 3C:
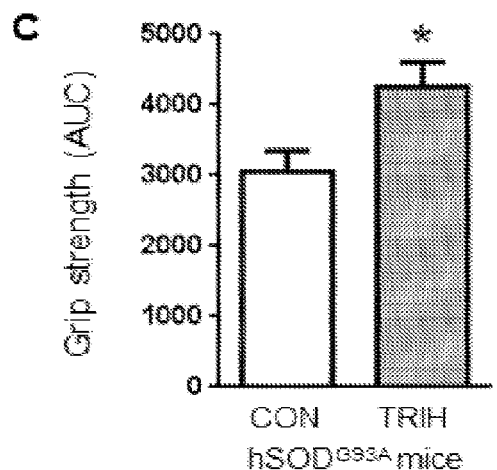
Figure 3D:
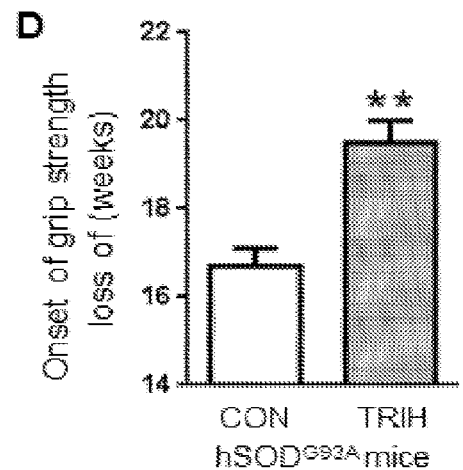
Figure 3E:
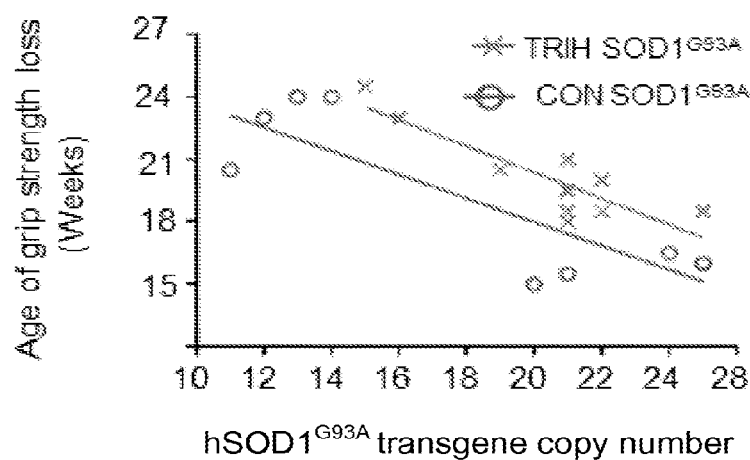
Figure 3F:
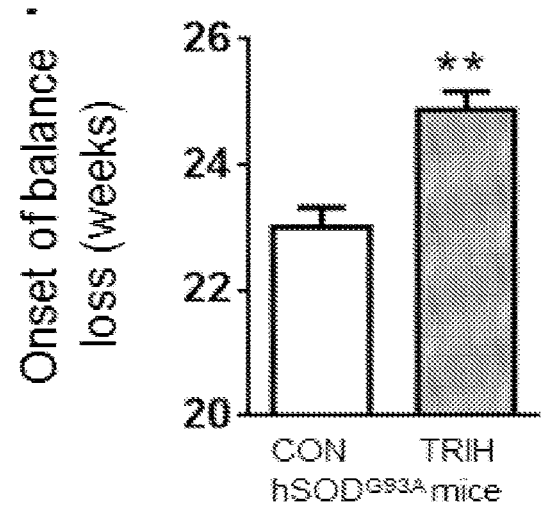
FIG. 3F depicts the onset of balance loss on the rota-rod (in weeks) in hSOD1$^{G93A}$ mice fed with control diet (CON) or triheptanoin (TRIH) diet. The data in FIG. 3F shows that the onset of balance loss in triheptanoin fed versus control fed SOD1$^{G93A}$ mice was significantly delayed by 13 days (p=0.0016).

For the following analyses, mice with only 12-17 copies of the SOD1 transgene were excluded from the analysis of grip strength and gene expression. Mice with 19-24 copies of the transgene were combined as one group with high copy transgene numbers. The grip strength of hSOD1$^{G93A}$ mice on both diets never exceeded 400 mN (FIG. 3B). The time course of reduced hind limb grip strength was significantly different between high copy number hSOD1$^{G93A}$ mice on the control diet (n=5) when compared to those on the triheptanoin diet (FIG. 3B, n=8; p=0.04, two way ANOVA). Bonferroni's multiple comparisons tests indicated that at 18 and 19.5 weeks of age, triheptanoin fed hSOD1$^{G93A}$ mice had higher hind limb grip strength when compared to control diet fed hSOD1$^{G9}$A mice (FIG. 3B, p<0.05). The area under the curve for the grip strength over time for each mouse on triheptanoin was increased by 38% relative to control diet (p=0.024, t-test, FIG. 3C). hSOD1$^{G93A}$ mice on the control diet began to lose hind limb grip strength at 16.5 weeks of age. The time of onset of the loss of hind limb grip strength was delayed by 2.8 weeks in hSOD1$^{G93A}$ mice fed triheptanoin (FIG. 3D). In the rotarod test, behavior of the hSOD1$^{G93A}$ mice varied widely, many mice seemed not to be "motivated" to learn how to balance on the rod and no satisfying presymptomatic baseline was reached. Therefore we could only assess the time point when mice were unable to stay on the rod. Triheptanoin delayed the time of onset of loss of balance by 1.6 weeks (p=0.0016; FIG. 3F).

Body weight loss and survival in hSOD1$^{G93A}$ mice with and without triheptanoin. Body weight is another indicator of disease progression in hSOD1$^{G93A}$ transgenic mice. When compared to wild-type mice on the control diet (n=12), wild-type mice on the triheptanoin diet (n=15) gained weight at a slower rate and were lighter when culled (p<0.0001, FIG. 3G). At 14 weeks of age, triheptanoin fed wild-type mice were approximately 3 g lighter than control fed wild-type mice (p<0.05). This weight difference increased to approximately 4 g at 22 weeks of age.

Figure 3G:
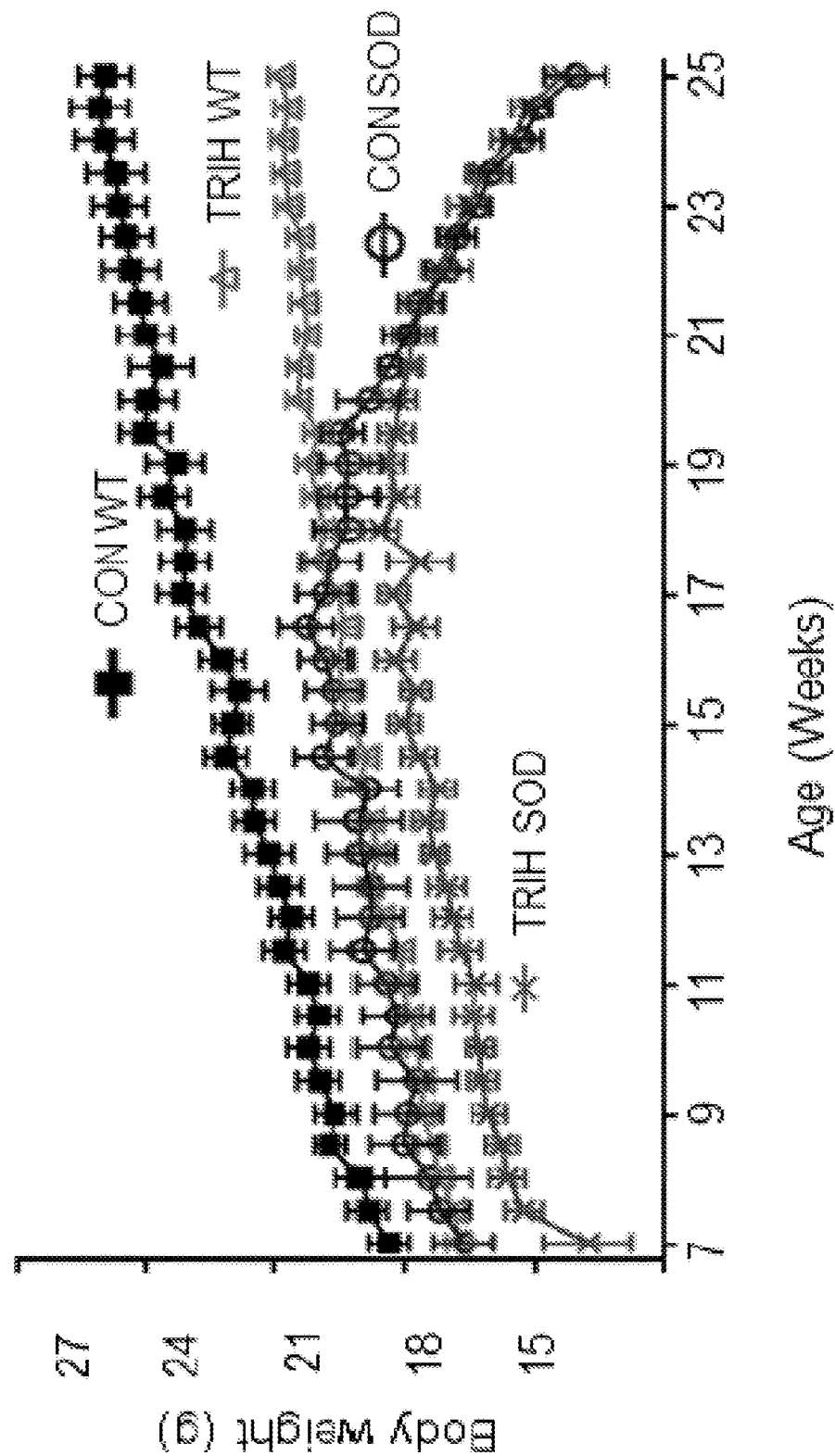
FIG. 3G depicts the body weights of wild-type (WT) or hSOD1$^{G93A}$ (SOD) mice fed with control diet (CON) or triheptanoin (TRIH) diet plotted against the ages of the mice. The data in FIG. 3G show that the body weights over time were significantly different between triheptanoin vs. control diet fed wild type mice and wild type mice on control diet vs. hSOD1$^{G93A}$ mice on either diet.
Figure 3H:
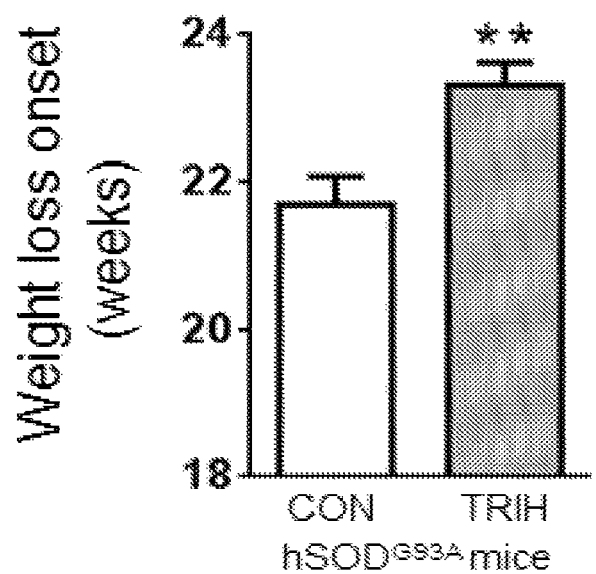
FIG. 3H depicts the weight loss onset of hSOD1$^{G93A}$ mice fed with control diet (CON) or triheptanoin (TRIH) diet. The data in FIG. 3H show that the onset of body weight loss in triheptanoin fed (n=8) compared to control fed SOD1$^{G93A}$ mice (n=5) was delayed by 11 days (p=0.0076, t-test). * p<0.05, ** p<0.01

Mice carrying 19-24 copies of the hSOD1 transgene on the control diet (n=5) and the triheptanoin diet (n=8) were lighter when compared to wild-type mice on the control diet (p<0.0001). There were no statistically significant differences between the hSOD1$^{G93A}$ transgenic mice on different diets over the full time period. However, compared to control diet, triheptanoin fed hSOD1$^{G93A}$ mice showed a trend of reduced body weight gain from 7-16 weeks. During the disease process after 20 weeks of age, the body weight of hSOD1$^{G93A}$ mice on the control and triheptanoin diet became similar (FIG. 3G). The onset of body weight loss in hSOD1$^{G93A}$ mice was delayed by triheptanoin feeding by 1.6 weeks (FIG. 3F, p=0.007, unpaired two-tailed t-test).

Only a small number of hSOD1$^{G93A}$ mice reached end-stage of disease, therefore our survival analysis is of limited power. No differences were seen in the number of days taken to reach end-stage when comparing triheptanoin (n=7) to control fed (n=5) hSOD1$^{G93A}$ mice (174.9±3.5 vs. 172.4±3.9, p=0.653), indicating that in this small study, triheptanoin treatment did not alter survival.

Figure 4:
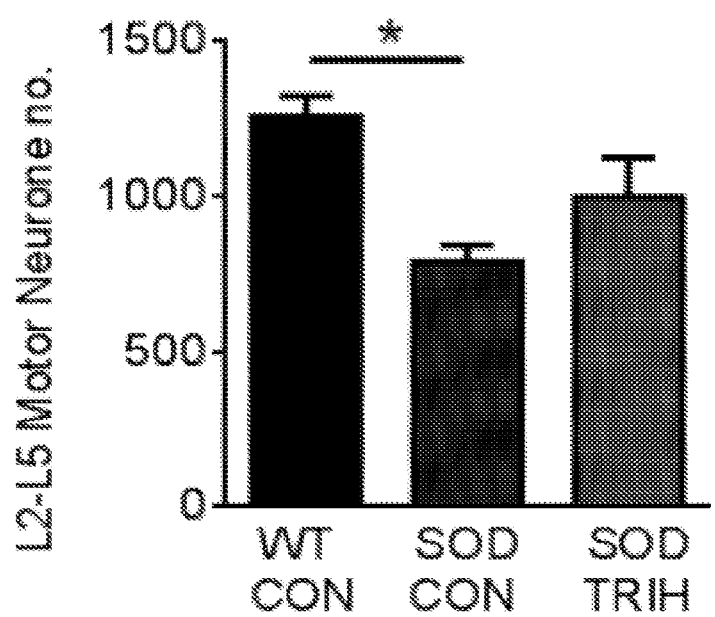
FIG. 4 depicts the result of motor neuron counting assay of 10 week old wild-type (WT) or hSOD1$^{G93A}$ (SOD) mice fed with control diet (CON) or triheptanoin (TRIH) diet. The data in FIG. 4 show that triheptanoin alleviated motor neuron death in hSOD1$^{G93A}$ mice fed triheptanoin (TRIH). The statistically significant loss of 37% of motor neurons between the L2 and L5 region in mice fed control diet (CON, n=3) is statistically insignificant in triheptanoin fed mice, showing 21% loss (n=4). Stereologic counts analysed by One Way ANOVAs followed by Tukey's multiple comparisons test.

Motor neuron counts. We assessed the number of motor neurons by stereological counting between L2 and L5 in mice at 70 days, which corresponds to onset of disease. The statistically significant loss of 37% of motor neurons in hSOD1$^{G93A}$ vs. wild type mice fed control diet (CON, n=3-4) was alleviated by feeding triheptanoin, as neuron numbers were not significantly different from wild type mice (n=4, FIG. 4).

Gene expression studies. To evaluate the extent to which TCA cycle metabolism or anaplerosis may be impaired in the gastrocnemius muscle of mid copy number hSOD1$^{G93A}$ mice at 10 weeks at symptom onset, quantitative real time PCR was used to compare the expression of genes involved in these pathways. The hSOD1$^{G93A}$ mice in the two diet groups had similar hSOD1$^{G93A}$ copy numbers, with 12-17 (average 14.4 copies) in the Con diet and 12-20 (average 15.75) copies in the triheptanoin-fed group (p=0.51 unpaired t-test). We chose to study the expression of enzymes involved in glycolysis (glyceraldehyde-3-phosphate dehydrogenase—Gapdh), the TCA cycle (2-oxoglutarate and succinate dehydrogenases, FIG. 5) and anaplerotic pathways of the muscle. The latter include pyruvate carboxylase (Pcx) producing oxaloacetate, glutamic pyruvic transaminase 1 and 2 (Gpt1 and 2, FIG. 5), and the enzymes of the propionyl-CoA carboxylation pathway (FIG. 6), namely the alpha and beta subunit of propionyl-carboxylase (Pcca and Pccb) and methylmalonyl mutase (Mut), which together metabolize propionyl-CoA to succinyl-CoA. Triheptanoin fed mice were included in this analysis to investigate if triheptanoin could alleviate any alterations observed.

Figure 5:
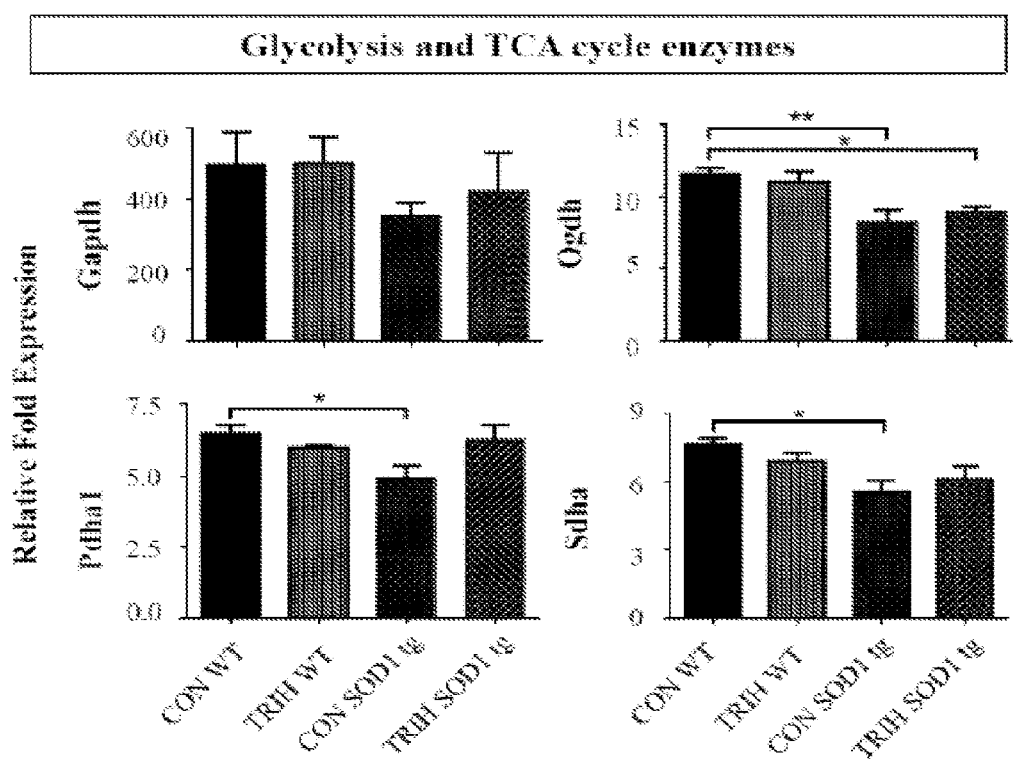
FIG. 5 depicts the result of a quantitative real time PCR analysis of Gapdh, Pdh alpha, Ogdh and Sdh subunit A mRNA of the gastrocneminus muscle of 10 week old wild type and hSOD1$^{G93A}$ mice fed control diet (CON) or triheptanoin (TRIH) relative to house keeping genes. Levels of transcripts of Pdhalpha1, OGDH and SDH subunit A were reduced in hSOD1$^{G93A}$ mice fed control diet (CON). These reductions in Pdhalpha1, and SDHalpha transcript levels were attenuated by triheptanoin feeding. One Way ANOVAs for each gene and time point, followed by Bonferroni post tests (* p<0.05, ** p<0.01) if significant.
Figure 6:
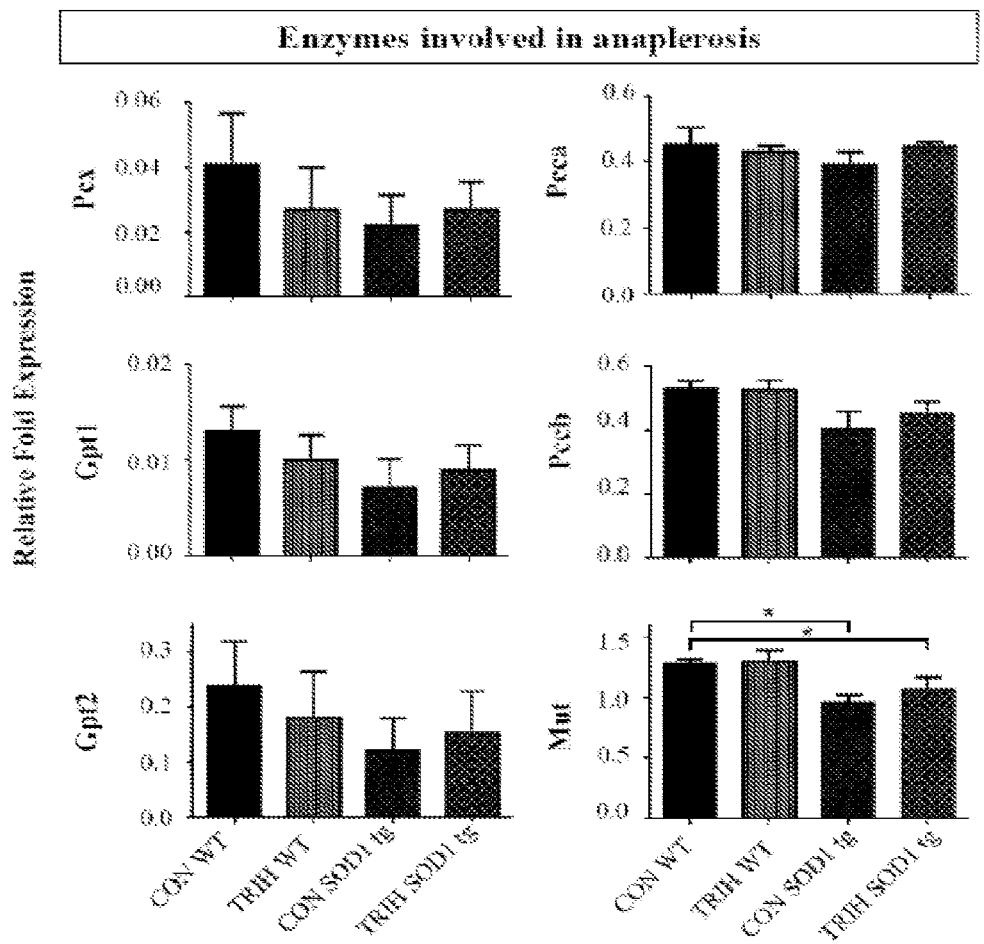
FIG. 6 depicts relative expression levels of genes involved in anaplerosis, specifically pyruvate carboxylase Pcx, glutamic pyruvic transferases Gpt1 and 2, the alpha (Pcca) and beta (Pccb) subunit of propionyl-CoA carboxylase and methyl-malonyl mutase (Mut). Expression is compared in the gastrocneminus muscle of 10 old wild type and hSOD1$^{G93A}$ mice fed control diet (CON) or triheptanoin (TRIH) relative to housekeeping genes. One Way ANOVAs for each gene and time point, followed by Bonferroni post tests (* p<0.05) if significant.

In 10 week old pre-symptomatic hSOD1$^{G93A}$ mice, quantitative real time PCR showed that when compared to wild-type mice, the expression of several dehydrogenases and methyl-malonyl mutase was reduced. Namely, we found statistically significant reductions for the mRNA levels of the A1 subunit of pyruvate dehydrogenase (Pdha1) by 24%, 2-oxoglutarate dehydrogenase (Ogdh) by 30%, the subunit A of succinate dehydrogenase (Sdha) by 23% and methyl-malonyl mutase (Mut) by 27.5% in hSOD1$^{G93A}$ mice (FIGS. 3, 5; all p<0.05 in post-test). Triheptanoin feeding protected hSOD1$^{G93A}$ mice from changes in the expression of pyruvate and succinate dehydrogenases, but not 2-oxo-glutarate dehydrogenase and methylmalonyl mutase. No alterations of mRNA levels were found in the other investigated genes, including glycolytic Gapdh and the genes involved in anaplerosis, Gpt1 and 2, Pcca and Pccb (FIGS. 5 and 6). Again triheptanoin feeding prevented some of the mRNA level reductions, indicating that it is effectively preserving the muscle and its metabolism.

Discussion

Effects of Triheptanoin and Clinical Importance

Figure 7:
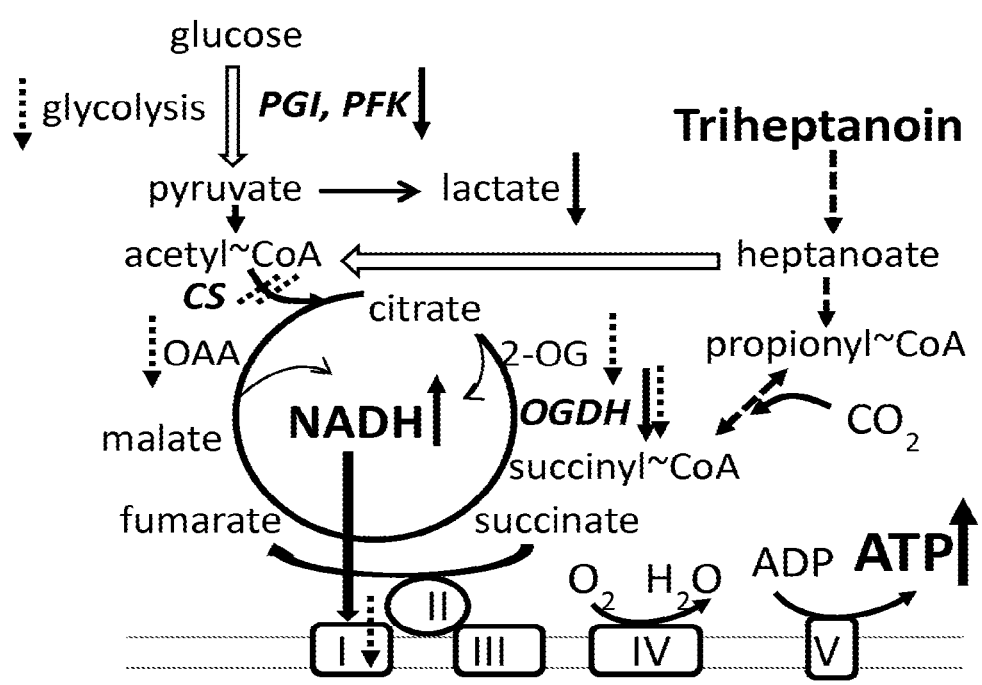
FIG. 7 illustrates metabolic alterations found in ALS patients and experimental mouse models and mechanisms of action of triheptanoin. In MND patients and mouse MND models, activities of glycolysis, citrate synthase (CS), oxoglutarate dehydrogenase (OGDH) (Russell et al., 2012), and complex I activity (Allen et al., 2014); as well as the levels (Niessen et al., 2007) of oxaloacetate (OAA) and 2-oxoglutarate (2-OG) are decreased (indicated with dotted arrows next to these enzymes or metabolites). Also, our findings of decreased maximal enzyme activities of PGI, PFK and OGDH in hSOD1$^{G93A}$ mice at mid disease (110-130 days) are indicated with solid arrows next to these enzymes. Triheptanoin is metabolised to propionyl-CoA and later to succinyl-CoA. This should increase 1) TCA cycle metabolite levels, 2) oxidation of acetyl-CoA and all fuels providing acctyl-CoA, 3) the number of electrons for electron transport chain complexes I & II, and 4) ATP production, resulting in improved survival of neurons and muscles.

One of the findings of this study is that hSOD1$^{G93A}$ mice show metabolic alterations (summarized in FIG. 7) in glycolysis and TCA cycle enzyme activity. These metabolic deficiencies can be mechanistically addressed by feeding triheptanoin, because it provides an alternative fuel to glucose and will improve TCA cycling and thereby oxidation of any fuel, including glucose.

Indeed, triheptanoin attenuated reductions in the gene expression of enzymes involved in TCA cycling and delayed symptoms of disease occurrence and disease progression in hSOD1$^{G93A}$ mice. This was observed as a delay in motor neuron death, in the onset of the loss in grip strength and loss of balance on the rotarod, a delay in the loss of body weight, and the reversal of the reduced expression of metabolism genes. Our data show a clear improvement in the condition of the hSOD1$^{G93A}$ mice in which triheptanoin feeding was initiated prior to the onset of disease symptoms. On the other hand, presymptomatic hSOD1$^{G93A}$ mice already show loss of crural flexor neurons (Ngo et al., 2012).

As a medium chain triglyceride, triheptanoin quickly provides heptanoic acid to the blood, which can enter all tissues and mitochondria by diffusion without involvement of carrier systems. Also, C5 ketones are quickly produced by the liver and they can enter most tissues via monocarboxylate transporters. Therefore, it is expected that anaplerosis via this pathway will begin quickly after treatment initiation.

Our power analyses regarding loss of grip strength and balance show that our study used adequate numbers of mice regarding these analyses of motor symptoms. From this our data show clear preservation of muscle function (disease modification) despite potential confounding effects on body weight. These data are very promising and warrant phase I clinical assessment of safety in ALS patients.

Metabolic Changes in hSOD1$^{G93A}$ Mouse Muscle

The decrease in lactate levels in muscle was interpreted as a decrease in glycolysis, because the level of lactate correlates strongly with those of pyruvate. We assumed that pyruvate levels are declined due to lowered activity of glycolytic enzymes PGI and PFK and in addition lowered activity of OGDH, which indicates slowing of the TCA cycle. Furthermore, our quantitative real time PCR data show that when compared to healthy wild-type mice, the expression of several enzymes involved in glycolysis, TCA cycle and anaplerosis were significantly reduced in the gastrocnemius muscle of hSOD1$^{G93A}$ mice at 10 weeks of age (FIGS. 5, 6) a time when hind limb grip strength is still normal (FIG. 3B). Taken together the specific downregulation of these enzymes suggest that TCA cycling is slowed in the muscle early before symptom onset and that insufficient ATP is produced for survival of tissue. Moreover, we found reduced mRNA levels of the main anaplerotic enzymes of muscle, the two glutamic pyruvic transaminases (gpt1 and 2), at 25 weeks, suggesting diminished levels of TCA cycle intermediates (data not shown).

In addition to slowing the disease process, triheptanoin prevented the downregulation of several enzymes which were reduced in the gastrocneminus muscles from hSOD1$^{G93A}$ when compared to wild-type mice. This finding implies that normalization of energy metabolism by triheptanoin may prevent downregulation of certain metabolism genes, which in turn will help to maintain a healthy metabolism to optimize energy supply and survival of tissue.

Conclusion

This study reveals that triheptanoin is a promising new treatment approach for ALS. Our data support initial clinical safety and tolerability trials of triheptanoin in ALS patients.

Throughout the specification, the aim has been to describe some embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety. To the extent that any definitions in documents incorporated by reference are inconsistent with the definitions provided herein, the definitions provided herein are controlling.

REFERENCES

Alexander G M, Erwin K L, Byers N, Deitch J S, Augelli B J, Blankenhorn E P, Heiman-Patterson T D. Effect of transgene copy number on survival in the G93A SOD1 transgenic mouse model of ALS. Brain Res Mol Brain Res 2004; 130: 7-15.

Allen S P, Rajan S, Duffy L, Mortiboys H, Higginbottom A, Grierson A J, Shaw P J. Superoxide dismutase 1 mutation in a cellular model of amyotrophic lateral sclerosis shifts energy generation from oxidative phosphorylation to glycolysis. Neurobiology of Aging 2014, 35:1499-1509.

Banks G B, Chau T N, Bartlett S E, Noakes P G. Promotion of motoneuron survival and branching in rapsyn-deficient mice. J Comp Neurol 2001, 429: 156-165.

Banks G B, Choy P T, Lavidis N A, Noakes P G. Neuromuscular synapses mediate motor axon branching and motoneuron survival during the embryonic period of programmed cell death. Dev Biol 2003, 257: 71-84.

Brunengraber H, Roe C R. Anaplerotic molecules: Current and future. J Inherit Metab Dis 2006; 29: 327-331.

Clarke P G H, Oppenheim R W. Neuron death in vertebrate development: in vivo methods. Methods Cell Biol. 1995, 46: 277-321. Cozzolino M, Carri M T. Mitochondrial dysfunction in ALS. Progr Neurobiol 2012; 97: 54-66.

Forgarty M J, Smallcombe, K L, Yanagawe, Y, Obata K, Bellingham M C, Noakes P G. Genetic deficiency of GABA differentially regulates respiratory and non-respiratory motor neuron development. Plos ONE 2013, 8: e56257

Gill A, Kidd J, Vieira F, Thompson K, Perrin S. No benefit from chronic lithium dosing in a sibling-matched, gender balanced, investigator-blinded trial using a standard mouse model of familial ALS. PLoS One 2009; 4: e6489.

Lai J C K and Cooper A J L. Brain α-Ketoglutarate Dehydrogenase Complex: Kinetic Properties, Regional Distribution, and Effects of Inhibitors. J. Neurochem 1986, 47, 1376-1386.

Milani P, Gagliardi S, Cova E, Cereda C. SOD1 Transcriptional and Posttranscriptional Regulation and Its Potential Implications in ALS. Neurology Res Int 2011; 2011: 458427.

Niessen H G, Debska-Vielhaber G, Sander K, Angenstein F, Ludolph A C, Hilfert L, Willker W, Leibfritz D, Heinze H J, Kunz W S, Vielhaber S Metabolic progression markers of neurodegeneration in the transgenic G93A-SOD1 mouse model of amyotrophic lateral sclerosis. European Journal of Neuroscience 2007, 25:1669-1677.

Ngo S T, Baumann F. Ridall P G, Pettitt A N, Henderson R D, Bellingham M C, McCombe P A. The relationship between Bayesian motor unit number estimation and histological measurements of motor neurons in wild-type and SOD1G93A mice. Clin Neurophysiol 2012; 123: 2080-2091.

Roe C R, Mochel F. Anaplerotic diet therapy in inherited metabolic disease: Therapeutic potential. J Inherit Metab Dis 2006; 29: 332-340.

Russell A P, Wada S, Vergani L, Hock M B, Lamon S, Leger B, Ushida T, Cartoni R, Wadley G D, Hespel P, Kralli A, Soraru G, Angelini C, Akimoto T Disruption of skeletal muscle mitochondrial network genes and miRNAs in amyotrophic lateral sclerosis. Neurobiology of Disease 2012, 49C:107-117.

Shi P, Wei Y, Zhang J, Gal J, Zhu H. Mitochondrial dysfunction is a converging point of multiple pathological pathways in amyotrophic lateral sclerosis. J Alz Dis 2010; 20 Suppl 2: S311-324.

Steyn F J, Ngo S T, Lee J D, Leong J W, Buckley A J, Veldhuis J D, McCombe P A, Chen C, Bellingham M C. Impairments to the GH-IGF-I Axis in hSOD1G93A Mice Give Insight into Possible Mechanisms of GH Dysregulation in Patients with Amyotrophic Lateral Sclerosis. Endocrinol 2012; 153: 3735-3746.

Thomas N K, Willis S, Swectman L, Borges K. Triheptanoin in acute mouse seizure models. Epilepsy Res 2012; 99: 312-317.

Turner B J, Talbot K. Transgenics, toxicity and therapeutics in rodent models of mutant SOD1-mediated familial ALS. Progr Neurobiol 2008; 85: 94-134.

Vandesompele J, De Preter K, Pattyn F, Poppe B, Van Roy N, De Paepe A, Speleman F. Accurate normalization of real-time quantitative RT-PCR data by geometric averaging of multiple internal control genes. Genome Biol 2002; 3: RESEARCH0034.

Vucic S, Kiernan M C. Pathophysiology of neurodegeneration in familial amyotrophic lateral sclerosis. Current molecular medicine 2009; 9: 255-272.

Wijesekera L C, Leigh P N. Amyotrophic lateral sclerosis. Orphanet J Rare Dis 2009; 4: 3.

The invention claimed is:

1. A method of treating amyotrophic lateral sclerosis (ALS) comprising administering to an animal with ALS a therapeutically effective amount of one or more precursors of propionyl-CoA, wherein the precursor of propionyl-CoA is selected from an uneven chain fatty acid, a triglyceride of an uneven chain fatty acid, a phospholipid comprising an uneven chain fatty acid, and a C5 ketone body.

2. The method of claim 1, wherein the triglyceride of an uneven chain fatty acid is selected from tripentanoin, triheptanoin and trinonanoin.

3. The method of claim 2, wherein the compound is triheptanoin.

4. The method of claim 1, wherein the one or more precursors of propionyl-CoA are provided to the animal in an amount comprising at least about 5% of the dietary caloric intake for the animal.

5. The method of claim 4, wherein the one or more precursors of propionyl-CoA are provided to the animal in an amount comprising at least about 20% of the dietary caloric intake for the animal.

6. The method of claim 5, wherein the one or more precursors of propionyl-CoA are provided to the animal in an amount comprising at least about 30% of the dietary caloric intake for the animal.

7. The method of claim 6, wherein the one or more precursors of propionyl-CoA are provided to the animal in an amount comprising at least about 35% of the dietary caloric intake for the animal.

8. The method of claim 1, wherein the animal is an adult animal.

9. The method of claim 1, wherein the animal is a mammal.

10. The method of claim 9, wherein the mammal is a human.

11. The method of claim 1, wherein the therapeutically effective amount of one or more precursors of propionyl-CoA is administered orally.

12. The method of claim 1, wherein the C5 ketone body is selected from p-hydroxypentanoate and β-ketopentanoate.

13. The method of claim 1, wherein the uneven chain fatty acid is selected from pentanoic acid, heptanoic acid, and nonanoic acid.

14. A method of treating amyotrophic lateral sclerosis (ALS) comprising administering to a subject with ALS a therapeutically effective amount of a seven carbon (C7) fatty acid source.

15. The method of claim 14, wherein the seven carbon (C7) fatty acid source is selected from triheptanoin, heptanoic acid, heptanoate, a triglyceride comprising heptanoic acid, and a triglyceride comprising heptanoic acid and a fatty acid other than heptanoic acid.

16. The method of claim 15, wherein the seven carbon (C7) fatty acid source is triheptanoin.

17. The method of claim 15, wherein the fatty acid other than heptanoic acid is selected from pentanoic acid and nonanoic acid.

18. The method of claim 16, wherein the triheptanoin is provided to the subject in an amount comprising at least about 20% of the dietary caloric intake for the subject.

19. The method of claim 16, wherein the triheptanoin is provided to the subject in an amount comprising at least about 30% of the dietary caloric intake for the subject.

20. The method of claim 14, wherein the subject is a human.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Mus sp.

<400> SEQUENCE: 1
agaattgcaa gggaaattgg                                               20

<210> SEQ ID NO 2
<211> LENGTH: 20
<212> TYPE: DNA
<213> ORGANISM: Mus sp.

<400> SEQUENCE: 2
ctaaagccat ccctggtctc                                               20

<210> SEQ ID NO 3
<211> LENGTH: 20
```

```
<212> TYPE: DNA
<213> ORGANISM: Mus sp.

<400> SEQUENCE: 3
agcctacaac atgctggaca                                              20

<210> SEQ ID NO 4
<211> LENGTH: 20
<212> TYPE: DNA
<213> ORGANISM: Mus sp.

<400> SEQUENCE: 4
ggtcctccca ttcattcttg                                              20

<210> SEQ ID NO 5
<211> LENGTH: 20
<212> TYPE: DNA
<213> ORGANISM: Mus sp.

<400> SEQUENCE: 5
ccaaacactg accgttctca                                              20

<210> SEQ ID NO 6
<211> LENGTH: 21
<212> TYPE: DNA
<213> ORGANISM: Mus sp.

<400> SEQUENCE: 6
ggaatgttta gctgcttcag g                                            21

<210> SEQ ID NO 7
<211> LENGTH: 20
<212> TYPE: DNA
<213> ORGANISM: Mus sp.

<400> SEQUENCE: 7
gagcttatcc cgaacatccc                                              20

<210> SEQ ID NO 8
<211> LENGTH: 21
<212> TYPE: DNA
<213> ORGANISM: Mus sp.

<400> SEQUENCE: 8
tccataccat tctctttggc c                                            21

<210> SEQ ID NO 9
<211> LENGTH: 20
<212> TYPE: DNA
<213> ORGANISM: Mus sp.

<400> SEQUENCE: 9
aacttctatg gaggcaacgg                                              20

<210> SEQ ID NO 10
<211> LENGTH: 20
<212> TYPE: DNA
<213> ORGANISM: Mus sp.

<400> SEQUENCE: 10
ctgaccctga ttagcagcac                                              20

<210> SEQ ID NO 11
```

-continued

```
<211> LENGTH: 20
<212> TYPE: DNA
<213> ORGANISM: Mus sp.

<400> SEQUENCE: 11
atacggctac agcaacaggg                                                   20

<210> SEQ ID NO 12
<211> LENGTH: 20
<212> TYPE: DNA
<213> ORGANISM: Mus sp.

<400> SEQUENCE: 12
tcttgctcag tgtccttgct                                                   20

<210> SEQ ID NO 13
<211> LENGTH: 20
<212> TYPE: DNA
<213> ORGANISM: Mus sp.

<400> SEQUENCE: 13
tgcagatgtg caatgatgac                                                   20

<210> SEQ ID NO 14
<211> LENGTH: 20
<212> TYPE: DNA
<213> ORGANISM: Mus sp.

<400> SEQUENCE: 14
gcagcacatg gaagaagttg                                                   20

<210> SEQ ID NO 15
<211> LENGTH: 22
<212> TYPE: DNA
<213> ORGANISM: Mus sp.

<400> SEQUENCE: 15
ggaacactcc aaaaacagac ct                                                22

<210> SEQ ID NO 16
<211> LENGTH: 23
<212> TYPE: DNA
<213> ORGANISM: Mus sp.

<400> SEQUENCE: 16
ccaccactgg gtattgagta gaa                                               23

<210> SEQ ID NO 17
<211> LENGTH: 20
<212> TYPE: DNA
<213> ORGANISM: Mus sp.

<400> SEQUENCE: 17
tgaggttatc cgtgccaata                                                   20

<210> SEQ ID NO 18
<211> LENGTH: 20
<212> TYPE: DNA
<213> ORGANISM: Mus sp.

<400> SEQUENCE: 18
gtccggactg ctcagaagat                                                   20
```

```
<210> SEQ ID NO 19
<211> LENGTH: 21
<212> TYPE: DNA
<213> ORGANISM: Mus sp.

<400> SEQUENCE: 19
gcgacggtat ttctacaatc c                                              21

<210> SEQ ID NO 20
<211> LENGTH: 20
<212> TYPE: DNA
<213> ORGANISM: Mus sp.

<400> SEQUENCE: 20
cgcggagtac aagggatact                                                20
```